US012668857B2

(12) United States Patent
Jansone-Popova et al.

(10) Patent No.: US 12,668,857 B2
(45) Date of Patent: Jun. 30, 2026

(54) METHODS FOR SEPARATION AND RECOVERY OF RARE EARTH ELEMENTS FROM AQUEOUS SOLUTIONS USING DIGLYCOLAMIDE DERIVATIVES

(71) Applicants: UT-Battelle, LLC, Oak Ridge, TN (US); Battelle Energy Alliance, LLC, Idaho Falls, ID (US)

(72) Inventors: Santa Jansone-Popova, Knoxville, TN (US); Kevin L. Lyon, Rigby, ID (US); Ilja Popovs, Knoxville, TN (US); Bruce A. Moyer, Oak Ridge, TN (US)

(73) Assignees: UT-Battelle, LLC, Oak Ridge, TN (US); Battelle Energy Alliance, LLC, Idaho Falls, ID (US)

( * ) Notice: Subject to any disclaimer, the term of this patent is extended or adjusted under 35 U.S.C. 154(b) by 539 days.

(21) Appl. No.: 17/366,185

(22) Filed: Jul. 2, 2021

(65) Prior Publication Data

US 2022/0002840 A1 Jan. 6, 2022

Related U.S. Application Data

(60) Provisional application No. 63/048,237, filed on Jul. 6, 2020.

(51) Int. Cl.
*C22B 59/00* (2006.01)
*B01D 11/04* (2006.01)
(Continued)

(52) U.S. Cl.
CPC .......... *C22B 59/00* (2013.01); *B01D 11/0492* (2013.01); *C01F 17/17* (2020.01);
(Continued)

(58) Field of Classification Search
None
See application file for complete search history.

(56) References Cited

U.S. PATENT DOCUMENTS 7,157,022 B2 1/2007 Horwitz et al.
8,354,085 B1 1/2013 Guelis
(Continued)

FOREIGN PATENT DOCUMENTS

AU 2019250770 A1 * 10/2020 .......... C07C 235/06
CN 101323906 A 12/2008
(Continued)

OTHER PUBLICATIONS

International Search Report and Written Opinion dated Dec. 23, 2021 issued in PCT/US21/40231, 8 pages.
(Continued)

*Primary Examiner* — Yun Qian
(74) *Attorney, Agent, or Firm* — Scully, Scott, Murphy & Presser, P.C.

(57) ABSTRACT

A method for extracting rare earth elements from aqueous solution, comprising: (i) acidifying an aqueous solution containing said rare earth elements with an inorganic acid to result in an acidified aqueous solution containing said rare earth elements and containing the inorganic acid in a concentration of 1-12 M, wherein said rare earth elements are selected from lanthanides, actinides, or combination thereof, and (ii) contacting the acidified aqueous solution with an aqueous-insoluble hydrophobic solution comprising a rare earth extractant compound dissolved in an aqueous-insoluble hydrophobic solvent to result in extraction of one or more of the rare earth elements into the aqueous-insoluble hydrophobic solution by binding of the rare earth extractant compound to the one or more rare earth elements, wherein the rare earth extractant compound has the following structure:

(Continued)

(1)

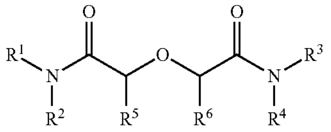

provided that at least one of the conditions (a)-(d) applies.

9 Claims, 11 Drawing Sheets

(51) Int. Cl.
*C01F 17/17* (2020.01)
*C07C 235/06* (2006.01)
*C07D 207/08* (2006.01)
*C07D 207/12* (2006.01)
*C07D 211/42* (2006.01)
*C22B 3/28* (2006.01)
*C22B 7/00* (2006.01)

(52) U.S. Cl.
CPC .......... *C07C 235/06* (2013.01); *C07D 207/08* (2013.01); *C07D 207/12* (2013.01); *C07D 211/42* (2013.01); *C22B 3/282* (2021.05); *C22B 7/007* (2013.01)

(56) References Cited

U.S. PATENT DOCUMENTS 9,968,887 B2 5/2018 Bhave et al.
11,040,296 B2 6/2021 Brigham et al.
2004/0062695 A1 4/2004 Horwitz et al.
2014/0072485 A1 3/2014 Luo et al.
2015/0292061 A1 10/2015 Fassbender et al.
2019/0287691 A1 9/2019 Abergel et al.
2019/0338394 A1 11/2019 Brown et al.
2019/0344198 A1 11/2019 Brigham et al.
2020/0122118 A1 4/2020 Jansone-Popova
2022/0002840 A1 1/2022 Jansone-Popova et al.
2022/0010409 A1 1/2022 Andreiadis et al.

FOREIGN PATENT DOCUMENTS

CN 106834680 A 6/2017
CN 106834757 A 6/2017
CN 106834758 A 6/2017
CN 106929675 A 7/2017
FR 2907346 A1 4/2008
FR 2948384 A1 1/2011
FR 2968014 A1 6/2012
JP 2004212076 A 7/2004
JP 2005201729 A 7/2005
JP 2006153790 A 6/2006
JP 2009132953 A 6/2009
JP 2011169888 A 9/2011
JP 2014105200 A 6/2014
JP 2016061580 A 4/2016
JP 2016065277 A 4/2016
JP 2018066709 A 4/2018
RU 2603405 C1 11/2016
WO 2011/012579 A1 2/2011
WO 2012/069573 A1 5/2012
WO 2015/076911 A2 5/2015
WO 2016/004770 A1 1/2016
WO 2016/182472 A1 11/2016
WO 2018/035020 A1 2/2018
WO 2019/197792 A1 10/2019

OTHER PUBLICATIONS

International Search Report and Written Opinion dated Oct. 13, 2021 issued in PCT/US 21/40229, 10 pages.
Stamberga, D., et al., "Structure Activity Relationship Approach toward the Improved Separation of Rare-Earth Elements Using Diglycolamides", Inorg. Chem. 2020, Received Sep. 25, 2020, Published Nov. 13, 2020, pp. 17620-17630, 59.
Office Action dated Nov. 7, 2024 received in U.S. Appl. No. 17/366,172, 23 pages.
Ravi J. et al., "New Unsymmetrical Digycolamide Ligands for Trivalent Actinide Separation", Radiochim. Acta 102 (7):609-617 (Mar. 19, 2014).
European Supplementary Extended Search Report dated Jun. 5, 2025 received in European Application No. 21 83 7547.5.
European Supplementary Extended Search Report dated Jun. 5, 2025 received in European Application No. 21 83 7748.9.

* cited by examiner (2A)

(2B)

(2C)

(2D)

(2E)

(2F)

(2G)

(2H)

(4B)

(4C)

METHODS FOR SEPARATION AND RECOVERY OF RARE EARTH ELEMENTS FROM AQUEOUS SOLUTIONS USING DIGLYCOLAMIDE DERIVATIVES

CROSS REFERENCE TO RELATED APPLICATION

The present application claims benefit of U.S. Provisional Application No. 63/048,237, filed on Jul. 6, 2020, all of the contents of which are incorporated herein by reference.

STATEMENT REGARDING FEDERALLY SPONSORED RESEARCH

This invention was made with government support under Prime Contract No. DE-AC05-00OR22725 and DE AC07-05-ID14517 awarded by the U.S. Department of Energy. The government has certain rights in the invention.

FIELD OF THE INVENTION

The present invention generally relates to rare earth-complexing ligands and their use in extracting rare earth elements (including lanthanides and/or actinides) from aqueous solutions into a hydrophobic aqueous-insoluble phase in which the ligand is dissolved. The present invention more particularly relates to diglycolamide derivatives as rare earth-extracting agents.

BACKGROUND OF THE INVENTION

Rare earth elements (REEs) generally include 15 lanthanides (lanthanum-lutetium), scandium, and yttrium. REEs possess unique physical and chemical properties and are integral for a variety of technology applications, ranging from energy generation to defense and military. The Department of Energy (DOE) and European Commission have named REEs as "critical raw materials" based on the challenges associated with their separation and continuous increase in global consumption (Sholl, D. S.; Lively, R. P. Seven chemical separations to change the world, *Nature* 2016, 533, 316-316; Critical Materials Strategy, Report DOE/PI-0009, U.S. Department of Energy, Washington, DC, December 2011). Lack of a domestic supply chain of pure REEs has left the United States dependent on other nations. Moreover, the low minable concentration of REEs in the Earth's crust makes it difficult to economically recover and separate them due to their very similar chemical and physical properties.

Solvent (liquid-liquid) extraction is the industry standard used to separate rare earth elements (REE) from aqueous acidic solutions. Liquid-liquid separation offers a continuous operation and sizable production capacity. The organophosphorus compound 2-ethylhexylphosphonic acid mono-(2-ethylhexyl) ester, also known under the common names EHEHPA or PC88A, is a well known extractant used industrially to separate the light REEs (lanthanum-gadolinium) from heavy REEs (yttrium, terbium-lutetium) as well as to purify individual elements. However, the adjacent lanthanide selectivity is quite low, with a reported selectivity for Nd over Pr in the REE(III)-HCl-EHEHPA system being just 1.17 (Xie, F. et al., *Minerals Engineering,* 2014, 56, 10-28). Another drawback of the EHEHPA process is the chemical nature and pH-swing mechanism by which the organophosphorus acids operate, which requires the consumption of acid and base via saponification to overcome the adverse liberation of acid encountered during REE extraction.

The diglycolamides (DGAs)—tridentate O-based neutral ligands—at first developed for actinide/lanthanide partitioning in the nuclear fuel cycle, have been investigated as effective alternatives to acidic extractants to achieve efficient separation of heavy REEs from light REEs (reported average adjacent-lanthanide separation factor for light REEs La—Pr in the REE(III)-HCl-TODGA system is 2.618). An advantage of these neutral ligands is that they do not require saponification, which results in less chemicals used and less waste produced. Some extensively studied diglycolamides include N,N,N,N'-Tetra(n-octyl)diglycolamide (TODGA), N,N,N',N'-tetra(2-ethylhexyl)diglycolamide (TEHDGA), and N,N-dimethyl-N',N'-di(n-octyl)diglycolamide (DMDODGA).

TEHDGA, having branched alkyl substituents on amide nitrogens, with the branching point close to the binding site, shows low affinity and selectivity across the lanthanide series, whereas TODGA (which has no branching) shows strong preference for heavy lanthanides, which results in acceptable separation of the light lanthanides, most notably, Nd/Pr. In addition, TODGA has higher separation factors than PC88A, which reduces stage requirements to facilitate separation. However, a substantial drawback of current diglycolamides is their tendency to form a third phase characterized by gelling/precipitation at higher diglycolamide concentrations/loading (above 0.1 M) in the organic phase and also generally requires consumption of large quantities of acid throughout the separation stages. There would be an advantage in a new extraction method that could effectively extract rare earth elements from acidic aqueous solutions while avoiding gelling or precipitation in the organic phase and without requiring consumption of large quantities of acid.

Another challenge is that REE sources from industrial byproduct streams (e.g., phosphoric acid production) often contain undesired material such as uranium and thorium. The economic viability of REE recovery from such streams is significantly hampered if material needs to be removed from the product stream. This is particularly true for the radioactive elements thorium and uranium. Moreover, REEs are critical components for many modern technologies, including those of renewable energy. To increase the domestic supply of REEs, new and more effective methods for extracting REEs from industrial byproduct streams are needed. There would also be an advantage in an extraction method that can remove one or more REEs more selectively than one or more other REEs, so as to permit a separation of REEs. There would be a further advantage in such a method using straight-forward and low-cost means for extraction and separation of REEs.

SUMMARY OF THE INVENTION

In a first aspect, the present disclosure is directed to diglycolamide-based compounds that can advantageously extract rare earth elements from acidic aqueous solutions with minimal or no formation of a third gelling or precipitation phase, and preferably, with sufficient or even greater separation ability than known extractant compounds. The extractant compound can preferably achieve this at higher extractant compound concentrations, e.g., of at least or above 0.1, 0.2, or 0.3 M. The rare earth extractant compounds described herein can also advantageously operate at lower acid concentrations than traditionally used in the art.

The rare earth extractant compound has the following structure:

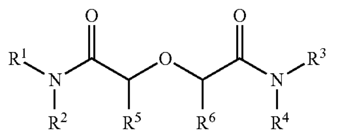

(1)

In Formula (1), $R^1$, $R^2$, $R^3$, and $R^4$ are independently selected from alkyl groups containing 1-30 carbon atoms and optionally containing an ether or thioether linkage connecting between carbon atoms, provided that the total carbon atoms in $R^1$, $R^2$, $R^3$, and $R^4$ is at least 12; $R^5$ and $R^6$ are independently selected from hydrogen atom and alkyl groups containing 1-3 carbon atoms; and provided that at least one of the following conditions apply:

Condition (i): at least one of $R^1$, $R^2$, $R^3$, and $R^4$ is a distal branched alkyl group constructed of a linear alkyl backbone having at least four carbon atoms with an alpha carbon atom of the linear alkyl backbone attached to a nitrogen atom shown in Formula (1), and the linear alkyl backbone contains a substituting hydrocarbon group at a gamma carbon or higher positioned carbon on the linear alkyl backbone, wherein the substituting hydrocarbon group contains at least one carbon atom, provided that the distal branched alkyl group contains a total of up to 30 carbon atoms;

Condition (ii): $R^1$ and $R^2$ are equivalent and $R^3$ and $R^4$ are separately equivalent, while $R^1$ and $R^2$ are different from $R^3$ and $R^4$, to result in an asymmetrical compound of Formula (1); or alternatively, only one of $R^1$, $R^2$, $R^3$, and $R^4$ is different, to result in an asymmetrical compound of Formula (1).

Condition (iii): $R^1$ and $R^2$ interconnect to form a first amine-containing ring, and/or $R^3$ and $R^4$ interconnect to form a second amine-containing ring, and the first and second amine-containing rings are attached to an alkyl group containing at least three carbon atoms and optionally containing an ether or thioether linkage connecting between carbon atoms, wherein the total number of carbon atoms in the first or second amine-containing ring and attached alkyl group is up to 30 carbon atoms; and/or Condition (iv): $R^2$ and $R^5$ interconnect to form a first lactam ring, and/or $R^4$ and $R^6$ interconnect to form a second lactam ring.

In a second aspect, the present disclosure is directed to a liquid solution useful for extracting rare earth elements (REEs) from an aqueous solution, typically an acidified aqueous solution. The liquid solution contains at least one rare earth extractant compound described above dissolved in an aqueous-insoluble (hydrophobic) solvent. The aqueous-insoluble hydrophobic solvent may be, for example, a hydrocarbon solvent. In some embodiments, the liquid solution further contains an organoamine soluble in the aqueous-insoluble hydrophobic solvent. The organoamine may contain at least one hydrocarbon group containing at least four carbon atoms. In other embodiments, the liquid solution further contains an alcohol soluble in the aqueous-insoluble hydrophobic solvent. The alcohol may contain at least six, seven, or eight carbon atoms.

In a third aspect, the present disclosure is directed to a method for extracting one or more rare earth elements from an aqueous solution. The method includes the following steps, at minimum: (i) acidifying an aqueous solution containing the one or more rare earth elements with an organic acid to result in an acidified aqueous solution containing the one or more rare earth elements and containing the inorganic acid in a concentration of 1-12 M, wherein the rare earth elements are selected from lanthanides, actinides, or combination thereof; and (ii) contacting the acidified aqueous solution with the aqueous-insoluble (hydrophobic) extractant solution described above to result in extraction of one or more of the rare earth elements into the extractant solution by binding of the rare earth extractant compound to the one or more rare earth elements. In some embodiments, the method further includes: (iii) stripping one or more rare earth elements from the extractant solution by contacting the extractant solution with an aqueous stripping solution of an inorganic acid wherein the inorganic acid is present in the aqueous stripping solution in a concentration of no more than 4 M, and provided that the concentration of inorganic acid in the aqueous stripping solution is at least 0.5 M less than the concentration of inorganic acid in the aqueous solution in step (i).

Notably, the extraction process described herein is advantageously straight-forward and cost-efficient while at the same time capable of removing a substantial portion or all of the REEs from an aqueous source, and further capable of separating REEs from each other by either selective extraction, selective stripping, or both. The extraction process can also advantageously extract rare earth elements from acidic aqueous solutions with minimal or no formation of a third gelling or precipitation phase, even when operated at higher extractant compound concentrations, such as at least 0.1 M, 0.2 M, 0.5 M, or 1 M. The above described extraction process can also advantageously operate at lower acid concentrations than traditionally used in the art, e.g., at 1-8 M or 2-6 M.

In some embodiments, the extraction solution exhibits a degree of selectivity in extracting the REEs, i.e., by extracting one or more REEs to a greater extent than one or more other REEs. In some embodiments, the extraction solution further includes an organoamine compound soluble in the aqueous-insoluble hydrophobic solvent, wherein the organoamine preferably contains at least one hydrocarbon group containing at least four carbon atoms. In alternative or further embodiments, the extractant solution further includes an alcohol soluble in the aqueous-insoluble hydrophobic solvent, wherein the alcohol preferably contains at least six carbon atoms.

DETAILED DESCRIPTION OF THE INVENTION

Figure 1:
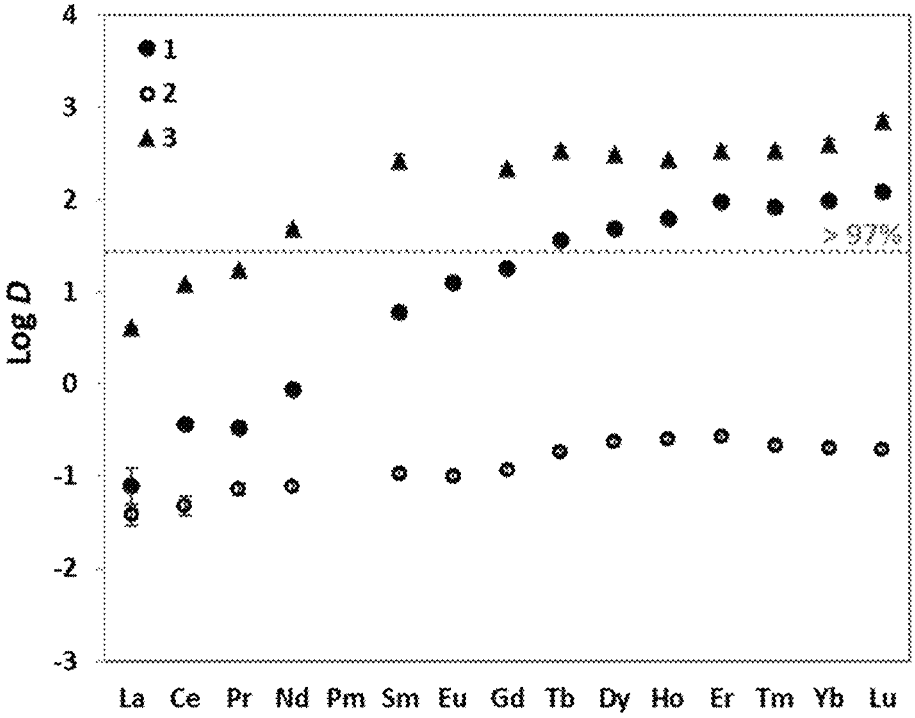
FIG. 1 is a graph plotting variation of log D in the extraction of Ln(III), 0.5 mM each, with 0.1 M DGA ligands 1 (TODGA), 2 (TEHDGA), and 3 (DMDODGA) from 3 M HCl media into Isopar L with 30 vol % of Exxal™ 13 at 25° C. after 1 hour. The dotted horizontal line represents the leveling off point.

As used herein, the term "hydrocarbon group" (also denoted by the group R) is defined as a chemical group composed solely of carbon and hydrogen, except that the hydrocarbon group may (i.e., optionally) be substituted with one or more fluorine atoms to result in partial or complete fluorination of the hydrocarbon group, or the hydrocarbon group may or may not also contain a single ether or thioether linkage connecting between carbon atoms in the hydrocarbon group. The hydrocarbon group typically contains 1-30 carbon atoms. In different embodiments, one or more of the hydrocarbon groups may contain, for example, 1, 2, 3, 4, 5, 6, 7, 8, 9, 10, 12, 15, 18, 20, 22, 24, 26, 28, or 30 carbon atoms, or a number of carbon atoms within a particular range bounded by any two of the foregoing carbon numbers (e.g., 1-30, 2-30, 3-30, 4-30, 6-30, 8-30, 10-30, 12-30, 1-20, 6-20, 8-20, 10-20, or 12-20 carbon atoms). Hydrocarbon groups in different compounds described herein, or in different positions of a compound, may possess the same or different number (or preferred range thereof) of carbon atoms in order to independently adjust or optimize such properties as the complexing ability, extracting (extraction affinity) ability, selectivity ability, or third phase prevention ability of the compound.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl, n-docosyl, n-tetracosyl, n-hexacosyl, n-octacosyl, and n-triacontyl groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl, isoheptyl, isooctyl, and the numerous other branched alkyl groups having up to 20 or 30 carbon atoms, wherein the "1-yl" suffix represents the point of attachment of the group.

In a third set of embodiments, the hydrocarbon group (R) is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2{=}CH{-}CH_2{-}CH_2{-}$), 2-buten-1-yl ($CH_2{-}CH{=}CH{-}CH_2{-}$), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 20 or 30 carbon atoms.

In a fifth set of embodiments, the hydrocarbon group (R) is unsaturated and branched, i.e., a branched olefinic or alkenyl group. Some examples of branched olefinic groups include propen-2-yl ($CH_2{=}C.{-}CH_3$), 1-buten-2-yl ($CH_2{=}C.{-}CH_2{-}CH_3$), 1-buten-3-yl ($CH_2{=}CH{-}CH.{-}CH_3$), 1-propen-2-methyl-3-yl ($CH_2{=}C(CH_3){-}CH_2{-}$), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 20 or 30 carbon atoms, wherein the dot in any of the foregoing groups indicates a point of attachment.

In a sixth set of embodiments, the hydrocarbon group (R) is unsaturated and cyclic, i.e., a cycloalkenyl group. The unsaturated cyclic group may be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems.

As indicated earlier above, any of the hydrocarbon groups described above may be substituted with one or more fluorine atoms. As an example, an n-octyl group may be substituted with a single fluorine atom to result in, for example, a 7-fluorooctyl or 8-fluorooctyl group, or substituted with two or more fluorine atoms to result in, for example, 7,8-difluorooctyl, 8,8-difluorooctyl, 8,8,8-trifluorooctyl, or perfluorooctyl group. As also indicated earlier above, any of the hydrocarbon groups described above may contain a single ether (—O—) or thioether (—S—) linkage connecting between carbon atoms in the hydrocarbon group. An example of a hydrocarbon group containing a single ether or thioether group is $-(CH_2)_2-X-(CH_2)_7CH_3$, wherein X represents O or S.

In one aspect, the present disclosure is directed to rare earth extractant compounds having an ability to complex with a rare earth element (i.e., REE) in solution and transfer (extract) the rare earth element from an aqueous solution into an aqueous-insoluble hydrophobic (non-polar) solution in which the extractant compound is dissolved. The extractant compound contains a diglycolamide moiety and at least one, two, three, or four hydrocarbon groups that render the diglycolamide molecule soluble in a non-polar aqueous-insoluble solvent, such as a hydrocarbon solvent. The term "compound" is herein meant to be synonymous with the term "molecule".

In particular embodiments, the extractant compound has a structure within the following generic structure:

(1)

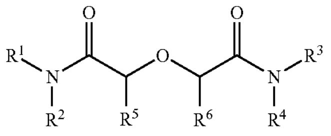

In Formula (1) above, $R^1$, $R^2$, $R^3$, and $R^4$ are independently selected from linear, branched, or cyclic alkyl groups (R') containing 1-30 carbon atoms, as described above, provided that the total carbon atoms in $R^1$, $R^2$, $R^3$, and $R^4$ (i.e., the sum of carbon atoms in all of $R^1$, $R^2$, $R^3$, and $R^4$) is at least 12. In different embodiments, the total carbon atoms in $R^1$, $R^2$, $R^3$, and $R^4$ is at least 12, 13, 14, 15, 16, 18, 20, 22, 24, 26, 28, 30, 32, 34, 36, 38, 40, 42, 44, 46, 48, 50, 52, 54, 56, 60, 64, 68, 70, 72, 76, or 80, or a total carbon number within a range bounded by any two of the foregoing values (e.g., 12-80). In some embodiments, $R^1$, $R^2$, $R^3$, and $R^4$ are the same, such as in the case where $R^1$, $R^2$, $R^3$, and $R^4$ are each isododecyl, i.e., $—(CH_2)_9CH(CH_3)_2$, in which case the total carbon number provided by $R^1$, $R^2$, $R^3$, and $R^4$ is 48. The term "same," as used herein, refers at least to the same carbon number in two or more of $R^1$, $R^2$, $R^3$, and $R^4$, and the term may further refer to the same structure. In other embodiments, at least one of $R^1$, $R^2$, $R^3$, and $R^4$ is different from another of $R^1$, $R^2$, $R^3$, and $R^4$, such as in the case where $R^1$ and $R^3$ are methyl groups and $R^2$ and $R^4$ are isooctyl groups (which results in a symmetric structure), or where $R^1$ and $R^2$ are methyl groups and $R^3$ and $R^4$ are isooctyl groups (which results in an asymmetric structure). In either of the foregoing cases, the total carbon number provided by $R^1$, $R^2$, $R^3$, and $R^4$ is 18. As noted in the above examples, the structure according to Formula (1) may be symmetric or asymmetric. Another example of an asymmetric structure is one in which $R^1$, $R^2$, and $R^3$ are equivalent to each other while different from $R^4$.

The groups $R^5$ and $R^6$ in Formula (1) above are independently selected from hydrogen atom and hydrocarbon groups containing 1-3 carbon atoms. In a first set of embodiments, $R^5$ and $R^6$ are hydrogen atoms. In a second set of embodiments, $R^5$ and $R^6$ are hydrocarbon groups containing 1-3 carbon atoms. In a third set of embodiments, one of $R^5$ and $R^6$ is a hydrogen atom and the other is a hydrocarbon group containing 1-3 carbon atoms. In the case where one or both of $R^5$ and $R^6$ is a hydrocarbon, the hydrocarbon is typically an alkyl group, typically containing 1-6 carbon atoms, and more particularly, a methyl, ethyl, n-propyl, or isopropyl group.

In some embodiments, $R^1$, $R^2$, $R^3$, and $R^4$ are all alkyl groups, which may be the same or different. A sub-class of Formula (1) in which $R^1$, $R^2$, $R^3$, and $R^4$ are all alkyl groups can be described by the following sub-formula:

(1a)

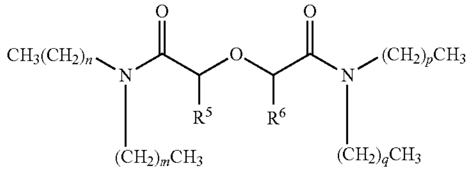

wherein m, n, p, and q are each independently an integer of 0-20, provided that the sum of m, n, p, and q is at least 8, and where $R^5$ and $R^6$ are as defined above. In some embodiments, m, n, p, and q are the same, such as m, n, p, and q all being 3, 4, 5, 6, 7, 8, 9, 10, 11, 12, 13, 14, 15, 16, 17, 18, or 19. In other embodiments, m, n, p, and q are not all the same, such as m and q being 0 and n and p each being 4, 5, 6, 7, 8, 9, 10, 11, 12, 13, 14, 15, 16, 17, 18, or 19; or, as another example, m and q being 1 or 2 and n and p each being 3, 4, 5, 6, 7, 8, 9, 10, 11, 12, 13, 14, 15, 16, 17, 18, or 19. Moreover, any one or more hydrogen atoms in methylene groups in Formula (1a) may optionally be replaced with a methyl, ethyl, n-propyl, or isopropyl group, to result in a branched hydrocarbon group, provided that the branched hydrocarbon group contains up to 20 carbon atoms, as provided in Formula (1).

Some examples of specific compounds under Formula (1a) in which all alkyl groups corresponding to $R^1$, $R^2$, $R^3$, and $R^4$ are the same are provided as follows:

(1a-1)

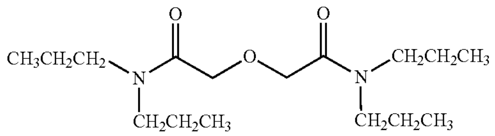

(1a-2)

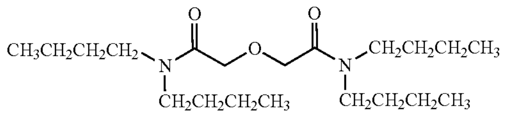

(1a-3)

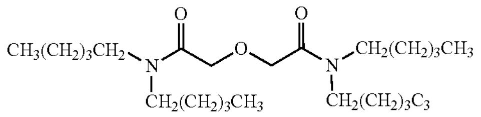

(1a-4)

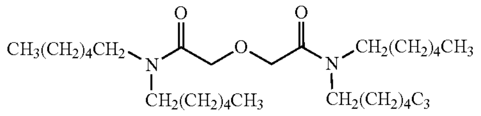

(1a-5)

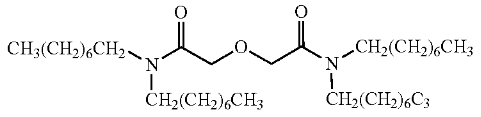

(1a-6)

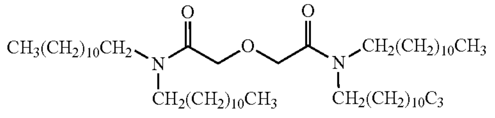

-continued (1a-7)

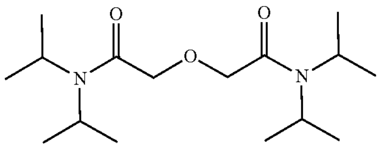

(1a-8)

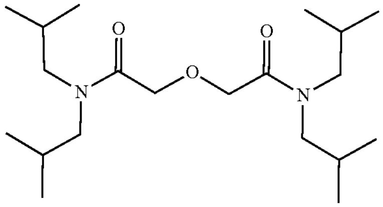

(1a-9)

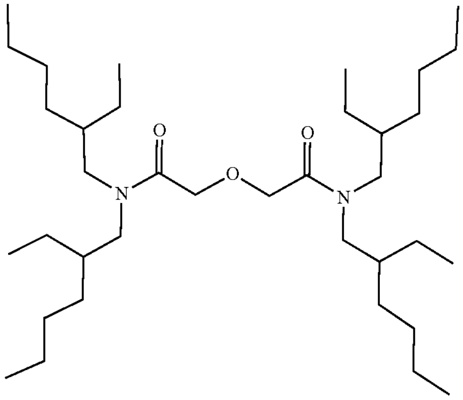

Some examples of specific compounds under Formula (1a) in which not all alkyl groups corresponding to $R^1$, $R^2$, $R^3$, and $R^4$ are the same are provided as follows:

(1a-10)

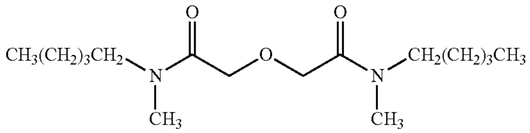

(1a-11)

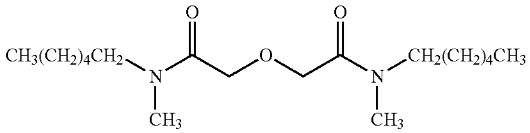

(1a-12)

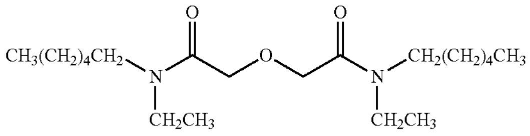

(1a-13)

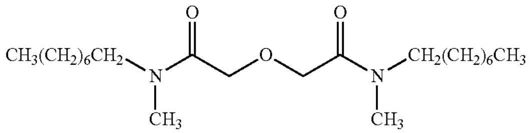

-continued (1a-14)

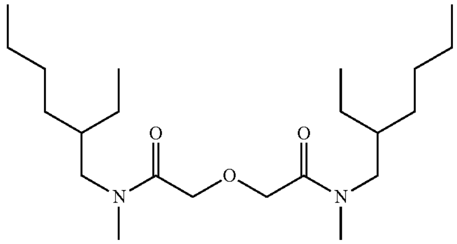

In some embodiments of Formula (1), a first condition applies in which at least one (e.g., one, two, three, or all) of $R^1$, $R^2$, $R^3$, and $R^4$ is a distal branched alkyl group constructed of a linear alkyl backbone having at least four, five, six, seven, eight, nine, ten, eleven, or twelve carbon atoms with an alpha carbon atom of the linear alkyl backbone attached to a nitrogen atom shown in Formula (1), and the linear alkyl backbone contains a substituting hydrocarbon group (which may be an alkyl group) at a gamma carbon or higher positioned carbon on the linear alkyl backbone. The substituting hydrocarbon group can be any of the hydrocarbon groups described above containing at least one or two carbon atoms, provided that the total number of carbon atoms in the distal branched alkyl group is up to 30 carbon atoms. In particular embodiments, one or more of the substituting hydrocarbon groups contain 1-6 carbon atoms, such as those selected from methyl, ethyl, n-propyl, isopropyl, n-butyl, isobutyl, sec-butyl, t-butyl, cyclopentyl, cyclohexyl, and phenyl groups. The linear alkyl backbone may be depicted as follows, with alpha, beta, gamma, delta, and epsilon positions denoted:

$$—(CH_2)_\alpha(CH_2)_\beta(CH_2)_\gamma(CH_2)_\delta(CH_2)_\varepsilon(CH_2)_n(CH_3),$$

wherein n is 0 or a number of 1 or greater. In some embodiments, the distal branched alkyl group contains precisely or at least one substituting hydrocarbon group located at a gamma carbon, delta carbon, epsilon carbon, or higher carbon position (e.g., zeta, eta, theta, iota, or kappa) of the linear alkyl backbone. In other embodiments, the distal branched alkyl group contains at least two (or more) substituting hydrocarbon groups independently located at a gamma carbon, delta carbon, epsilon carbon, or higher carbon position (e.g., zeta, eta, theta, iota, or kappa) or combination of such positions of the linear alkyl backbone.

Some examples of distal branched alkyl groups according to condition 1 include:

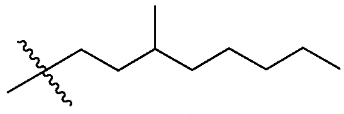

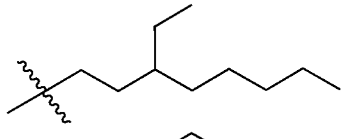

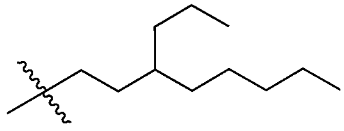

-continued

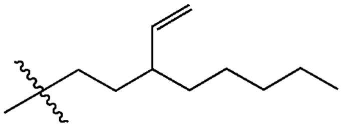

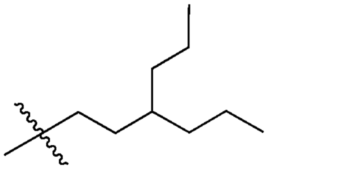

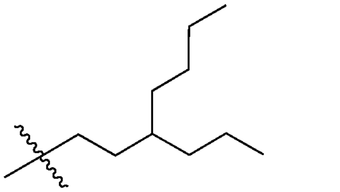

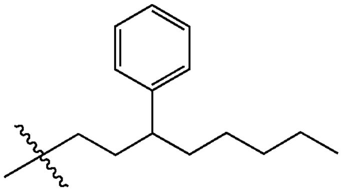

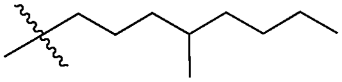

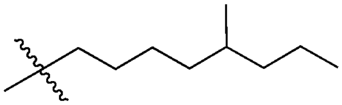

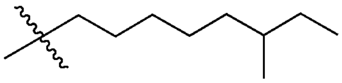

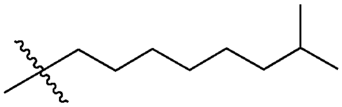

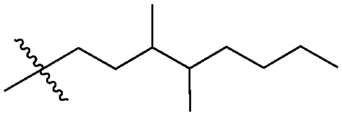

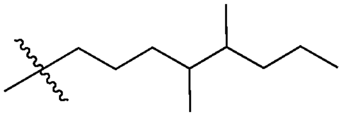

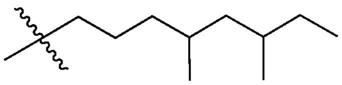

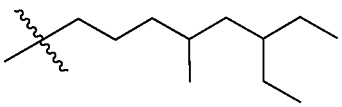

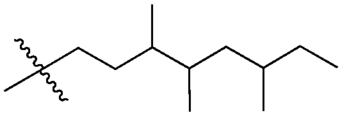

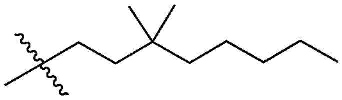

-continued

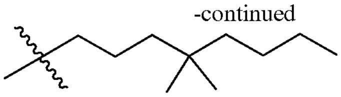

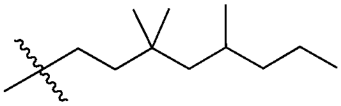

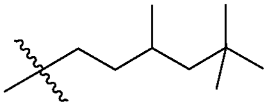

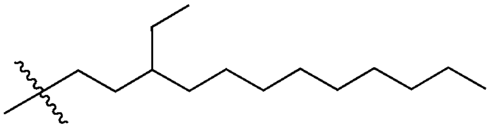

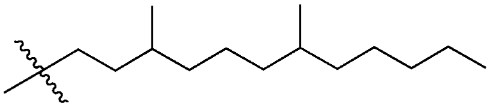

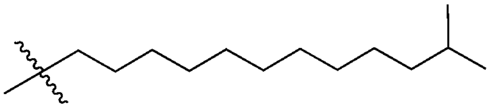

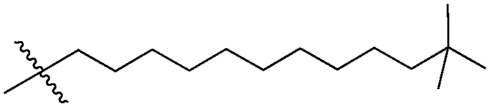

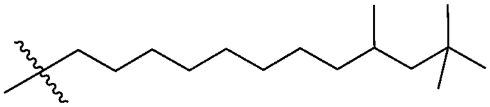

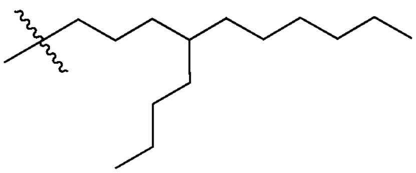

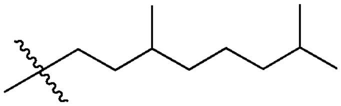

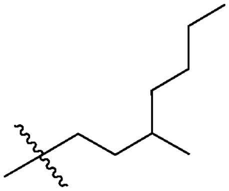

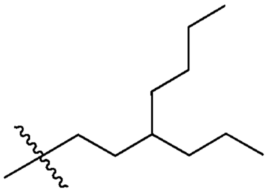

The compounds according to Formula (1) and sub-formulas thereof can be synthesized by methods well known in the art. Reference is made to, for example, D. D. Dicholkar et al., *Ind. Eng. Chem. Res.,* 52(7), 2457-2469, 2013, which describes the synthesis of N,N,N',N'-tetraoctyl-3-oxapentane-1,5-diamide (TODGA) in detail. The Examples, provided later below, describe a number of methods for producing these compounds.

In some embodiments of Formula (1), a second condition applies in which $R^1$ and $R^2$ are equivalent and $R^3$ and $R^4$ are separately equivalent, while $R^1$ and $R^2$ are different from $R^3$ and $R^4$, to result in an asymmetrical compound of Formula (1). In some embodiments, $R^1$ and $R^2$ are equivalent hydrocarbon groups (or more particularly, alkyl groups) containing 1-3 carbon atoms, and $R^3$ and $R^4$ are separately equivalent hydrocarbon groups containing 4-30, 6-30, 8-30, 10-30, 12-30, 4-20, 6-20, 8-20, 10-20, or 12-20 carbon atoms, wherein all such hydrocarbon groups have been described above. For example, $R^1$ and $R^2$ may both be methyl or ethyl and $R^3$ and $R^4$ may both be the same $C_3$-$C_{30}$, $C_4$-$C_{30}$, $C_5$-$C_{30}$, $C_6$-$C_{30}$, $C_7$-$C_{30}$, or $C_8$-$C_{30}$, linear, branched, or cyclic alkyl group, as described above, such as n-propyl, isopropyl, cyclopropyl, n-butyl, sec-butyl, isobutyl, t-butyl, cyclobutyl, n-pentyl, isopentyl, n-hexyl, isohexyl, cyclohexyl, n-octyl, isooctyl, n-decyl, n-undecyl, n-dodecyl, n-tetradecyl, n-hexadecyl, or larger group with or without substitution with one or more hydrocarbon groups (R) as described above. Alternatively, only one of $R^1$, $R^2$, $R^3$, and $R^4$ is different to result in an asymmetrical compound. For example, $R^1$ may be methyl or ethyl and $R^2$, $R^3$, and $R^4$ may all be the same $C_3$-$C_{30}$, $C_4$-$C_{30}$, $C_5$-$C_{30}$, $C_6$-$C_{30}$, $C_7$-$C_{30}$, or $C_5$-$C_{30}$, linear, branched, or cyclic alkyl group, as described above, such as n-propyl, isopropyl, cyclopropyl, n-butyl, sec-butyl, isobutyl, t-butyl, cyclobutyl, n-pentyl, isopentyl, n-hexyl, isohexyl, cyclohexyl, n-octyl, isooctyl, n-decyl, n-undecyl, n-dodecyl, n-tetradecyl, n-hexadecyl, or larger group with or without substitution with one or more hydrocarbon groups (R) as described above. Any of the alkyl groups described above may or may not contain fluorine substitution and/or an ether or thioether linkage connecting between carbon atoms.

In some embodiments of Formula (1), a third condition applies in which $R^1$ and $R^2$ interconnect to form a first amine-containing ring, and/or $R^3$ and $R^4$ interconnect to form a second amine-containing ring. The first and second amine-containing rings are typically attached to at least one alkyl group containing at least three, four, five, six, seven, or eight carbon atoms (and up to 12, 18, 20, 24, or 30 carbon atoms), wherein the alkyl group optionally contains fluorine substitution and optionally contains an ether or thioether linkage connecting between carbon atoms. The total number of carbon atoms in the first or second amine-containing ring and attached alkyl group (combined) is typically up to 30 carbon atoms. The amine-containing ring is typically a five-membered or six-membered ring. The amine-containing ring may be substituted with an additional hydrocarbon group (R), such as any of those described above, particularly alkyl groups containing 1-4 carbon atoms, such as a methyl, ethyl, n-propyl, isopropyl group. n-butyl, sec-butyl, isobutyl, or t-butyl group. Some examples of extractant compounds according to the third condition of Formula (1) include:

(1b-1)

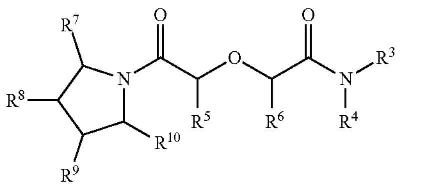

-continued (1b-2)

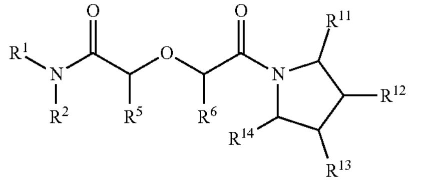

(1b-3)

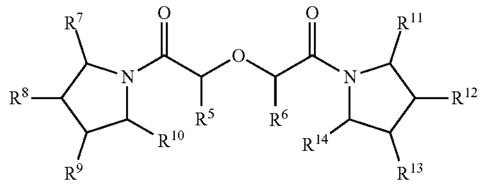

In the above structures (1b-1), (1b-2), and (1b-3), $R^7$, $R^8$, $R^9$, $R^{10}$, $R^{11}$, $R^{12}$, $R^{13}$, and $R^{14}$ are independently selected from hydrogen atom (H) and hydrocarbon groups (R) described earlier above, provided that at least one of $R^7$, $R^8$, $R^9$, $R^{10}$, $R^{11}$, $R^{12}$, $R^{13}$, and $R^{14}$ is a hydrocarbon group (R) containing 1-30 carbon atoms. In some embodiments, at least one of $R^7$, $R^8$, $R^9$, $R^{10}$, $R^{11}$, $R^{12}$, $R^{13}$, and $R^{14}$ is an alkyl group containing 1-30 carbon atoms. In some embodiments, at least one of $R^7$, $R^8$, $R^9$, $R^{10}$, $R^{11}$, $R^{12}$, $R^{13}$, and $R^{14}$ is a methyl, ethyl, n-propyl, or isopropyl group. In some embodiments, at least one of $R^7$, $R^8$, $R^9$, $R^{10}$, $R^{11}$, $R^{12}$, $R^{13}$, and $R^{14}$ is a hydrocarbon group (or more particularly, an alkyl group) containing 4-30, 6-30, 8-30, 10-30, 12-30, 4-20, 6-20, 8-20, 10-20, or 12-20 carbon atoms. In particular embodiments, $R^9$ and/or $R^3$ is a hydrocarbon group, or more particularly an alkyl group, containing 1-30 carbon atoms or any of the particular sub-ranges of carbon atoms provided above.

In some embodiments of Formula (1), a fourth condition applies in which $R^2$ and $R^5$ interconnect to form a first lactam ring, and/or $R^4$ and $R^6$ interconnect to form a second lactam ring. The lactam ring is typically a five-membered or six-membered ring. The lactam ring may also be substituted with any of the hydrocarbon groups (R) described above containing 1-30 carbon atoms, including methyl, ethyl, n-propyl, and isopropyl groups. Some examples of extractant compounds according to the fourth condition of Formula (1) include:

(1c-1)

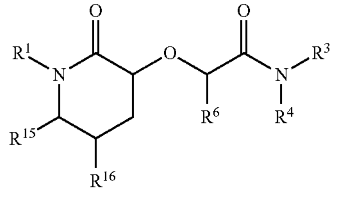

(1c-2)

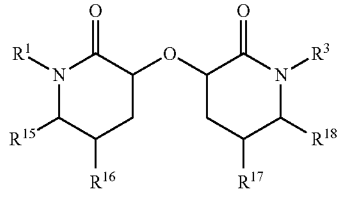

-continued (1c-3)

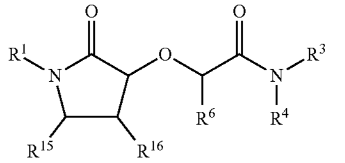

(1c-4)

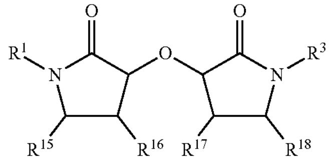

In the above structures (1c-1), (1c-2), (1c-3), and (1c-4), $R^{15}$, $R^{16}$, $R^{17}$, and $R^{18}$ are independently selected from hydrogen atom (H) and hydrocarbon groups (R) described earlier above. In some embodiments, at least one, two, three, or all of $R^{15}$, $R^{16}$, $R^{17}$, and $R^{18}$ are hydrogen atoms. In other embodiments, precisely or at least one of $R^{15}$, $R^{16}$, $R^{17}$, and $R^{18}$ is a hydrocarbon group (R) or more particularly a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms). In typical embodiments, at least one (or both) of $R^1$ and $R^3$ in the above structures (1c-1), (1c-2), (1c-3), and (1c-4) is a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms). In other embodiments, at least one (or all) of $R^1$, $R^3$, and $R^4$ is a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms).

In another aspect, the present disclosure is directed to a liquid extractant solution useful for extracting rare earth elements from aqueous solutions. The extraction solution includes one or more extractant compounds (i.e., any one or more of the diglycolamide compounds of Formula (1) or sub-formulas thereof or species thereof, described above), dissolved in an aqueous-insoluble hydrophobic solvent. The aqueous-insoluble hydrophobic solvent can be any of the hydrophobic organic solvents known in the art that are substantially or completely immiscible with water or aqueous solutions in general. The aqueous-insoluble hydrophobic solvent is typically a hydrocarbon solvent, which may be non-halogenated (e.g., hexanes, heptanes, octanes, decanes, dodecanes, benzene, toluene, xylenes, kerosene, or petroleum ether), or halogenated (e.g., methylene chloride, chloroform, carbon tetrachloride, 1,2-dichlorethane, trichloroethylene, and perchloroethylene), or etherified (e.g., diethyl ether or diisopropyl ether), or combination of halogenated and etherified (e.g., bis(chloroethyl)ether and 2-chloroethyl vinyl ether). In some embodiments, the extractant solution is composed solely of the extractant compound and the aqueous-insoluble hydrophobic solvent. In other embodiments, the extractant solution contains one or more additional components, as further discussed below. The one or more extractant compounds may be present in the extractant solution in a concentration of, for example, precisely, at least, or up to, for example, 0.01 M, 0.02 M, 0.05 M, 0.1 M, 0.2 M, 0.3 M, 0.4 M, 0.5 M, 0.6 M, 0.7 M, 0.8 M, 0.9 M, or 1 M or a concentration within a range bounded by any two of the foregoing values, e.g., 0.01-1 M, 0.01-0.5 M, 0.05-1 M, 0.05-0.5 M, 0.1-1 M, 0.1-0.8 M, 0.1-0.5 M, 0.2-1 M, 0.2-0.8 M, or 0.2-0.5 M.

In some embodiments, the extractant solution, as described above, further includes an organoamine soluble in the aqueous-insoluble hydrophobic solvent. The organoamine may function to, for example, further bind to the REE, prevent or lessen formation of a third phase during the extraction, and/or assist in removing (stripping) the REE from the aqueous-insoluble hydrophobic solvent after extraction. To be soluble in the hydrophobic solvent, the organoamine should be sufficiently hydrophobic (lipophilic). To be sufficiently hydrophobic, the organoamine should contain at least one hydrocarbon group containing at least four carbon atoms. However, to ensure full solubility of the organoamine in the hydrophobic solvent, the organoamine preferably contains, in total, at least or more than six carbon atoms. In different embodiments, the organoamine may contain at least or more than, for example, 6, 7, 8, 9, 10, 11, 12, 13, 14, 15, 16, 17, 18, 19, or 20 carbon atoms, or a number of carbon atoms within a range bounded by any two of the foregoing values. The organoamine may be a primary, secondary, or tertiary amine. Some examples of primary organoamines include n-hexylamine, isohexylamine, n-heptylamine, n-octylamine, isooctylamine, n-nonylamine, n-decylamine, n-undecylamine, n-dodecylamine, n-tridecylamine, n-tetradecylamine, and n-hexadecylamine. Some examples of secondary organoamines include dibutylamine, diisobutylamine, dipentylamine, dihexylamine, diheptylamine, diooctylamine, dinonylamine, didecylamine, didodecylamine, N-methylbutylamine, N-methylpentylamine, N-methylhexylamine, N-methylheptylamine, N-methyloctylamine, N-ethylbutylamine, and N-ethyloctylamine. Some examples of tertiary organoamines include tributylamine, tripentylamine, trihexylamine, triheptylamine, trioctylamine, trinonylamine, tridecylamine, triundecylamine, and tridodecylamine.

In some embodiments, the extractant solution, as described above, further includes an organoamide soluble in the aqueous-insoluble hydrophobic solvent. The organoamide may function to, for example, further bind to the REE, prevent formation of a third phase during the extraction, and/or assist in removing (stripping) the REE from the aqueous-insoluble hydrophobic solvent after extraction. To be soluble in the hydrophobic solvent, the organoamide should be sufficiently hydrophobic (lipophilic). To be sufficiently hydrophobic, the organoamide should contain at least one hydrocarbon group containing at least four carbon atoms. However, to ensure full solubility of the organoamide in the hydrophobic solvent, the organoamide preferably contains, in total, at least or more than six carbon atoms. In different embodiments, the organoamide may contain at least or more than, for example, 6, 7, 8, 9, 10, 11, 12, 13, 14, 15, 16, 17, 18, 19, or 20 carbon atoms, or a number of carbon atoms within a range bounded by any two of the foregoing values. Some examples of hydrophobic organoamides include N-methylpentanamide, N-ethylpentanamide, N-propylpentanamide, N-butylpentanamide, N-pentylpentanamide, N-hexylpentanamide, N-methylhexanamide, N-ethylhexanamide, N-propylhexanamide, N-methyloctanamide, N-ethyloctanamide, N-propyloctanamide, N-methyldecanamide, N-ethyldecanamide, N-propyldecanamide, N,N-dimethylpentanamide, N,N-diethylpentanamide, N,N-dipropylpentanamide, N,N-dibutylpentanamide, N,N-dihexylpentanamide, and N,N-diethyloctanamide.

In some embodiments, the extractant solution, as described above, further includes an alcohol soluble in the aqueous-insoluble hydrophobic solvent. The alcohol generally functions to prevent or lessen formation of a third phase during the extraction. To be soluble in the hydrophobic solvent, the alcohol should be sufficiently hydrophobic (lipophilic). To be sufficiently hydrophobic, the alcohol typically contains at least or more than six carbon atoms. In different embodiments, the alcohol contains at least or more than, for example, 6, 7, 8, 9, 10, 11, 12, 13, 14, 15, 16, 17, 18, 19, or 20 carbon atoms, or a number of carbon atoms within a range bounded by any two of the foregoing values. Some examples of lipophilic alcohols include n-hexyl alcohol, 4-methyl-1-pentanol, n-heptanol, n-octanol, 6-methyl-1-heptanol, 2-ethyl-1-hexanol, n-decanol, n-dodecanol, n-tridecanol, isotridecanol, n-tetradecanol, and n-hexadecanol.

In another aspect, the present disclosure is directed to a method for extracting one or more rare earth elements from an aqueous source solution containing the one or more rare earth elements. The term "rare earth element" or "rare earth metal," as used herein, refers to at least the lanthanide elements (elements having an atomic number of 57-71). The rare earth elements may or may not also include scandium (Sc) and yttrium (Y). The rare earth elements may or may not also include one or more of the actinide elements (elements having an atomic number of 90-103).

At least one lanthanide element is typically present in the aqueous source solution. The one or more lanthanide elements present in the aqueous source solution may include one or more of the following elements: lanthanum (La), cerium (Ce), praseodymium (Pr), neodymium (Nd), promethium (Pm), samarium (Sm), europium (Eu), gadolinium (Gd), terbium (Th), dysprosium (Dy), holmium (Ho), erbium (Er), thulium (Tm), ytterbium (Yb), and lutetium (Lu). In the aqueous source solution, the rare earth elements are present in ionic form (e.g., $Nd^{+3}$) and salt form (e.g., $Nd_2(SO_4)_3$). The aqueous source solution may also contain at least one (or one or more) of any of the actinide elements, such as uranium (U) and/or thorium (Th). In some embodiments, one or more of any of the foregoing rare earth elements are not present in the aqueous source solution.

In a first step of the extraction process (i.e., step (i)), the aqueous source solution is acidified with an inorganic acid (mineral acid) to result in an acidified aqueous source solution containing the rare earth elements and containing the inorganic acid in a concentration of 1-12 M. In different embodiments, the inorganic acid concentration of the aqueous source solution is precisely or about, for example, 1, 2, 3, 4, 5, 6, 7, 8, 9, 10, 11, or 12 M, or an inorganic acid concentration within a range bounded by any two of the foregoing values (e.g., 1-12 M, 2-12 M, 2-8 M, 2-6 M, 3-12 M, 1-8 M, 2-8 M, 3-8 M, 1-5 M, 2-5 M, 3-5 M, or 1-3 M), wherein the term "about" may correspond to ±50%, ±20%, or ±10% of any of the foregoing values. The inorganic acid may be, for example, a hydrohalide (i.e., HX, wherein X is typically Cl, Br, or I), sulfuric acid ($H_2SO_4$), nitric acid ($HNO_3$), or phosphoric acid ($H_3PO_4$). In some embodiments, one or more of the foregoing inorganic acids is excluded from the acidified aqueous source solution. In particular embodiments, the inorganic acid is hydrochloric acid or hydrobromic acid, which may or may not be combined with another inorganic acid.

In a second step of the extraction process (i.e., step (ii)), the acidified aqueous source solution from step (i) is contacted with the above-described aqueous-insoluble hydrophobic extracting solution containing a diglycolamide compound of Formula (1). The term "contacted" or "contacting," as used herein in reference to contacting of the aqueous and organic phases, generally refers to an intimate mixing of the aqueous and organic phases so as to maximize extraction of the one or more rare earth elements from the aqueous phase to the organic phase. Methods of intimately mixing liquids are well known in the art. For example, the aqueous and organic phases may be placed in a container and the container agitated. In some embodiments, the liquids are intimately mixed by subjecting them to vortex mixing. Following mixing, the two phases are generally separated by means well known in the art, such as by standing or centrifugation. The foregoing described process amounts to an efficient liquid-liquid extraction process whereby one or more rare earth elements in the aqueous source solution is/are extracted, in some cases selectively, into the aqueous-insoluble hydrophobic solvent (organic phase).

The extraction process is generally capable of achieving a distribution coefficient (D), which may also herein be referred to as an extraction affinity, of at least 1 for one or more the rare earth elements, wherein D is the concentration ratio of the rare earth element in the organic phase divided by its concentration in the aqueous phase. In some embodiments, a D value of greater than 1 is achieved, such as a D value of at least or above 2, 5, 10, 20, 50, 100, 150, 200, 250, 500, or 1000. The selectivity of the process can be characterized by the separation factor (SF), wherein SF is calculated as the ratio of D for two different ions, such as any two of the ions disclosed above, such as selectivity of an earlier lanthanide (e.g., Nd) relative to one or more later lanthanides (e.g., Tb), in which particular case $SF=D_{Nd}/D_{Tb}$. Selectivity is generally evident in an SF value greater than 1. In some embodiments, an SF value of at least or greater than 2, 5, 10, 20, 50, 100, 150, 200, 250, 500, or 1000 is achieved.

In some embodiments, the extraction step (step ii) extracts one or more rare earth elements to a greater degree (i.e., by a greater D value) than one or more other rare earth elements. By extracting one or more elements to a greater degree than one or more elements, the extraction step is exhibiting a degree in selectivity. The degree of selectivity can be adjusted by, for example, selection of the extracting molecule according to Formula (1); selection of the concentration of the extracting molecule in the hydrophobic solution; and selection of the inorganic acid and acid concentration in the aqueous source solution. For example, depending on the foregoing conditions employed, the extraction step may extract one or more early lanthanide elements (e.g., La, Ce, Pr, and/or Nd) to a lesser or greater extent (i.e., at a lower D value or higher D value, respectively) than one or more later lanthanide elements (e.g., Sm, Eu, Gd, Tb, Dy, Ho, Er, Tm, Yb, and/or Lu) or Y. As another example, the extraction step may extract one or more lanthanide elements to a greater extent than one or more actinide elements (e.g., Th and/or U), or vice-versa.

In some embodiments, the extraction method described above further includes a successive stripping step (step (iii)). In the stripping step, one or more rare earth elements contained in the aqueous-insoluble hydrophobic solution is contacted with an aqueous stripping solution containing at least one inorganic acid, such as any of the inorganic acids described above, wherein the inorganic acid is typically present in a concentration of no more than 4 M. Generally, the concentration of inorganic acid in the aqueous stripping solution is at least 0.5 M less (or at least 1 M, 1.5 M, 2 M, 3M, or 4M less) than the concentration of inorganic acid in the aqueous source solution in step (i). In different embodiments, inorganic acid concentration in the stripping solution is precisely, about, up to (no more than), or less than, for example, 4 M, 3.5 M, 3 M, 2.5 M, 2 M, 1.5 M, 1 M, 0.5 M, 0.25 M, 0.1 M, 0.05 M, 0.02 M, or 0.01 M, or a concentration within a range bounded by any two of the foregoing values (e.g., 0.01-4 M, 0.01-3 M, 0.01-2 M, 0.01-1 M, 0.01-0.5 M, 0.01-0.2 M, or 0.01-0.1M). Typically, the lower acid concentration in the stripping solution favors removal (extraction) of lighter lanthanides over heavier lanthanides and actinides (from the hydrophobic solution into the stripping solution).

Examples have been set forth below for the purpose of illustration and to describe certain specific embodiments of the invention. However, the scope of this invention is not to be in any way limited by the examples set forth herein.

EXAMPLES

Diglycolamide (DGA) Based Compounds as Rare Earth Metal Extractants

In the following experiments, ligands are described that have a high affinity for lanthanide elements, herein denoted as Ln(III) elements, that operate at higher ligand concentrations, such as 0.5 M, without forming a third-phase gel or precipitate and that operate at lower acid concentrations, e.g., 1-3 M. The superior performance of these ligands results in significant cost savings. Moreover, these novel ligands can be used in a solid phase for liquid-solid separation schemes, such as chromatographic separations.

The following extractant compounds were studied, while noting that TODGA, TEHDGA, and DMDODGA are well known compounds that have been included for comparative purposes:

1

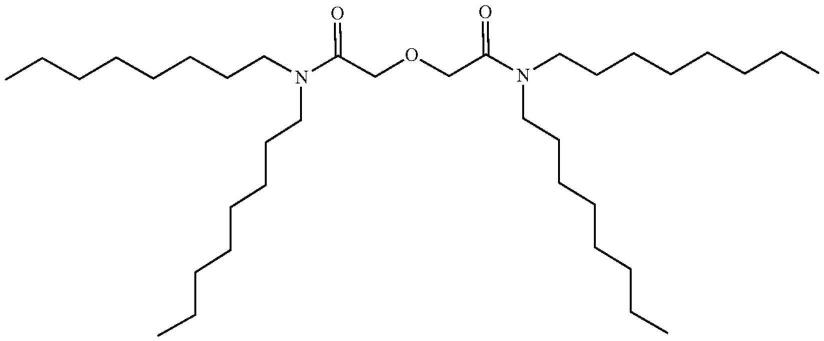

(TODGA)

2

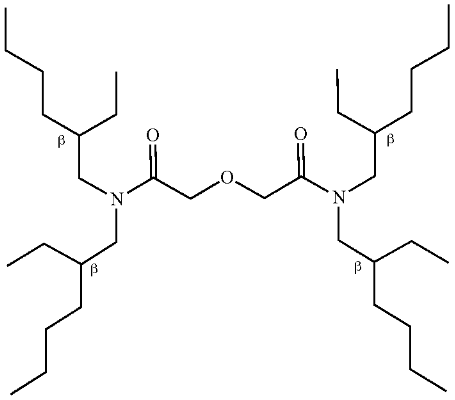

(TEHDGA)

3

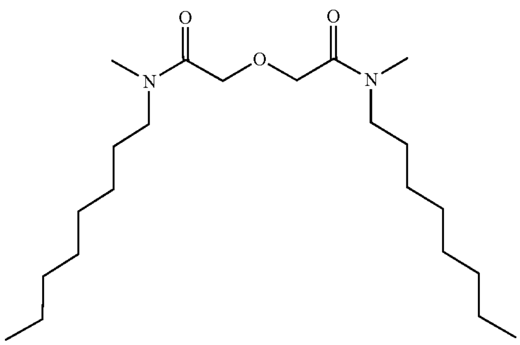

(DMDODGA)

-continued
4
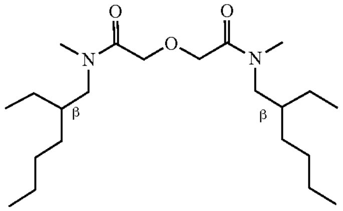
5
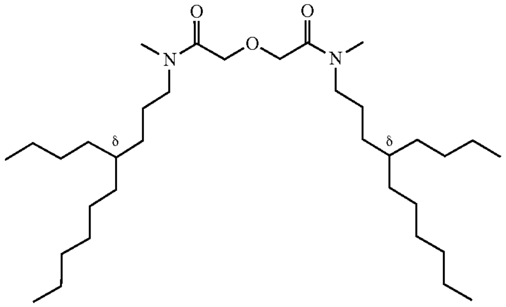
6
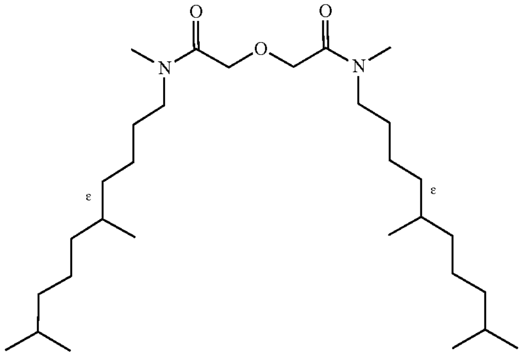
7
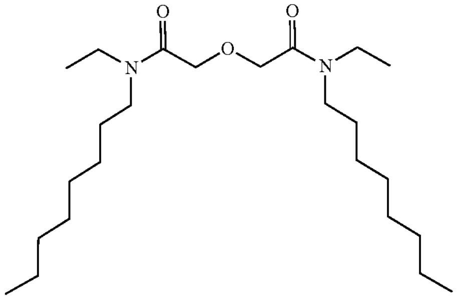
8
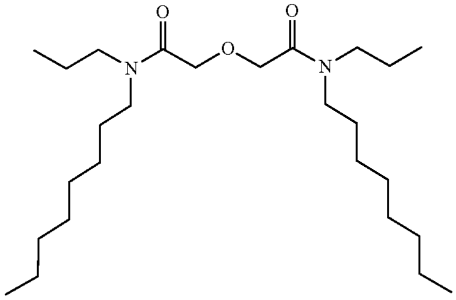
9
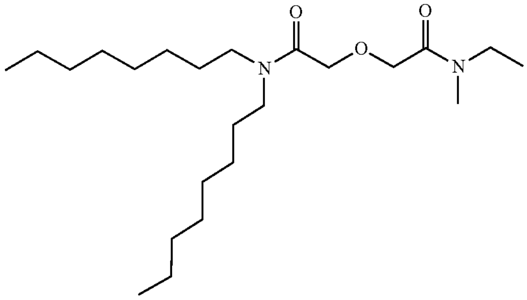
10
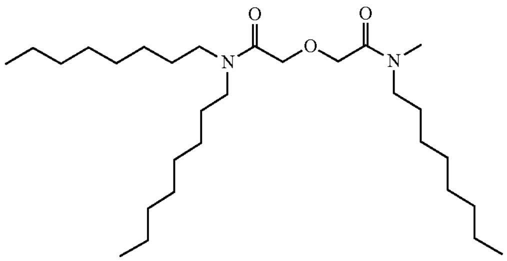
11
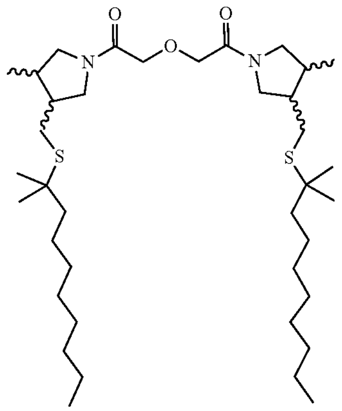

-continued
12
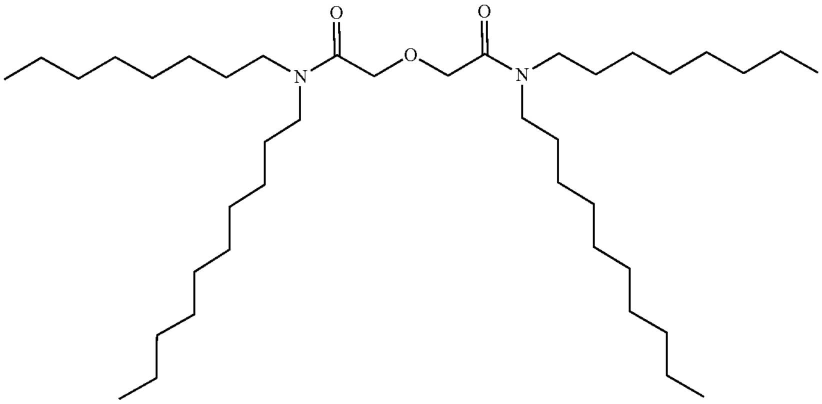
13
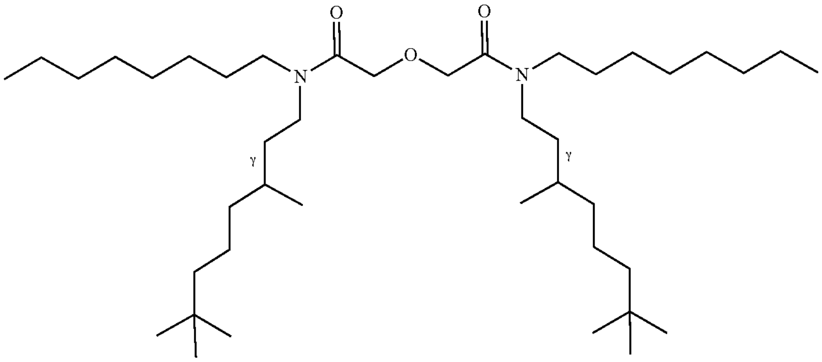
14
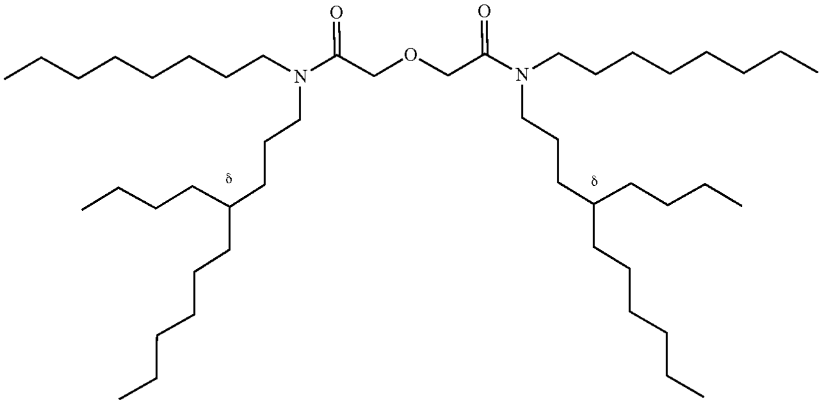
15
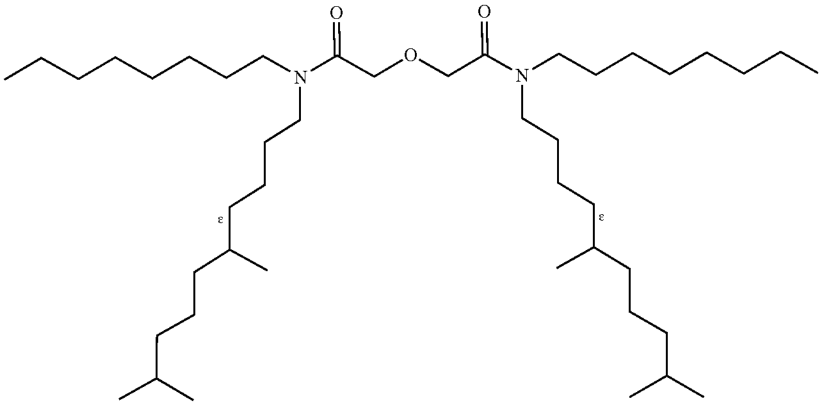

-continued
16
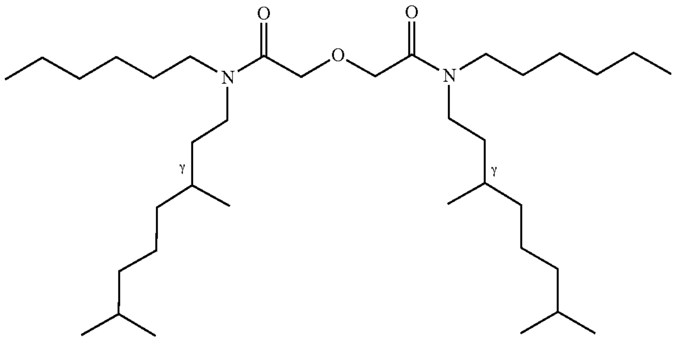
17
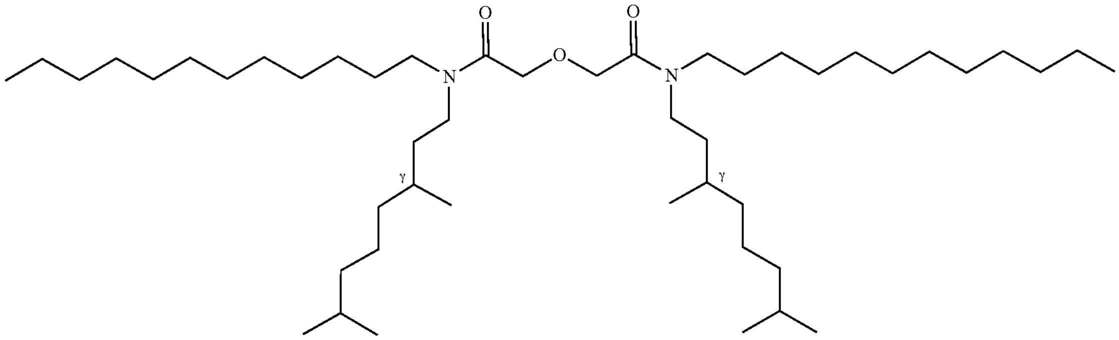
18
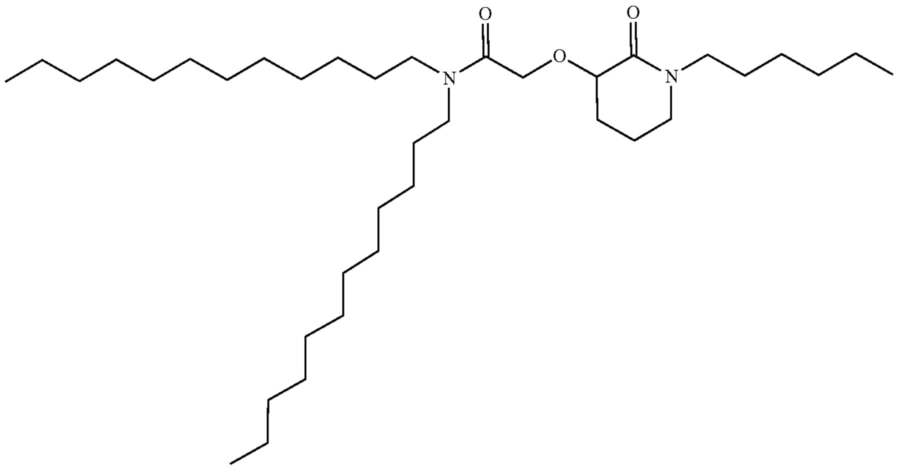
19
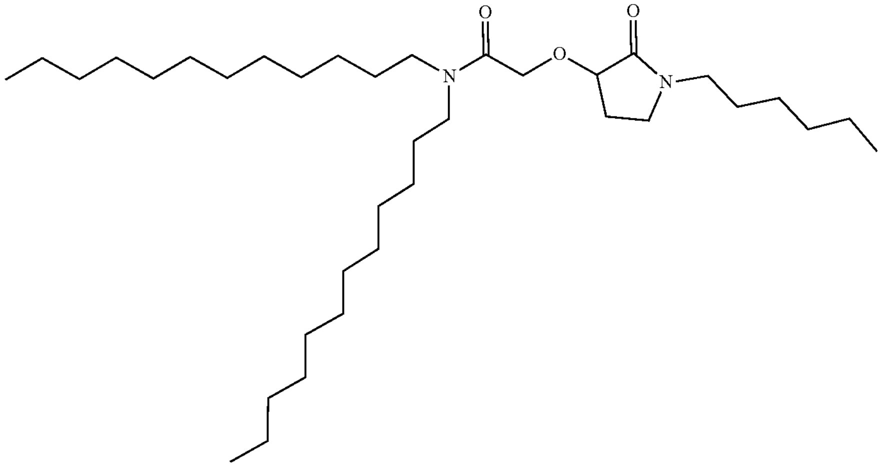

-continued

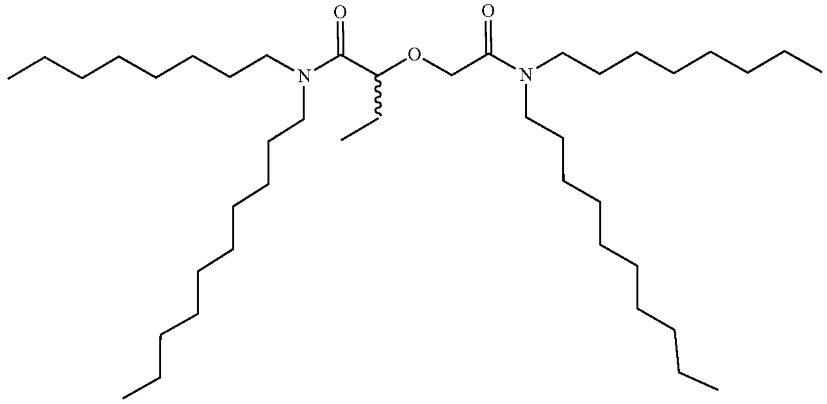

Synthesis of Extractant Compounds

DGA ligands 4-17 were synthesized using the following synthetic protocol:

a)

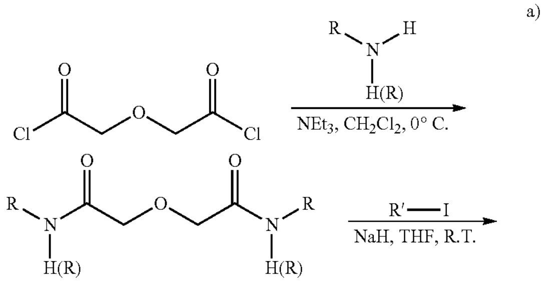

9, 10, 13, 16, 17

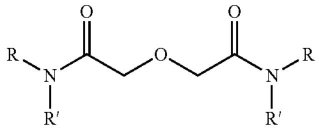

4-8, 12, 14, 15 b)

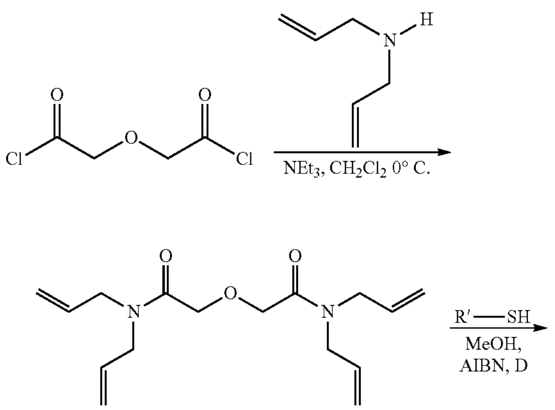

-continued

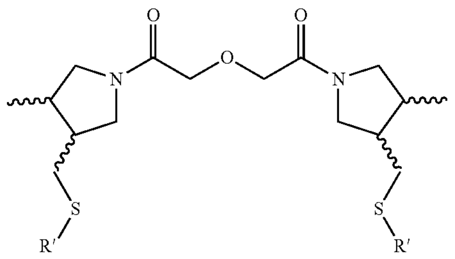

11

The above scheme (a) shows synthesis of extractant compounds with linear and branched N-alkyl substituents. The above scheme (b) shows synthesis of extractant compounds containing pyrrolidine rings. In the above schemes, diglycolyl chloride was reacted with 1° or 2° amine to produce either di- or tetra-substituted DGA, respectively. The di-substituted DGAs were further functionalized using alkyl iodide as an alkylating agent and sodium hydride as a base to produce tetra-substituted DGAs. Furthermore, a novel strategy was included that reduces steric crowding around the metal ion binding site by converting linear N,N'-alkyl substituents into a five-membered pyrrolidine, which is represented by DGA ligand 11. Compound 11 was synthesized by free radical induced addition of alkylthiol (R'—SH) to N,N'-diallyl substituted DGA, as shown in scheme (b).

Detailed Synthesis for Compounds 4-8, 12, and 14-18

The following general synthetic scheme was used:

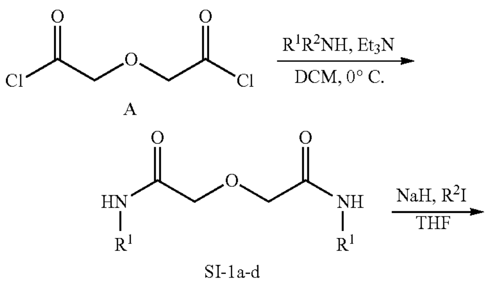

A

SI-1a-d

-continued

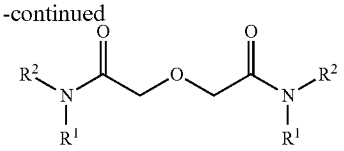

4-8, 12, 14-17

General procedure for the synthesis of N,N'-monosubstituted 2,2'-oxybisacetamide ligands SI-1a-d: Compounds SI-1a-d were prepared following this procedure. In a round-bottom flask equipped with a stir bar, an amine (2.1 equiv.) was combined with anhydrous $CH_2Cl_2$ (0.2 M) and $Et_3N$ (2.1 equiv.). The reaction mixture was cooled in an ice-water bath prior to slow addition of 2,2-oxydiacetyl chloride A (1 equiv.). The reaction mixture was allowed to warm up to room temperature and stir for 1 hour. Afterwards, $Et_2O$ (~0.1 M) was added in one portion, the precipitate was removed via filtration through a short Celite® plug and rinsed with $Et_2O$ (3×) to yield crude product. See below for additional details.

2,2'-oxybis(N-(2-ethylhexyl)acetamide) SI-1a was synthesized according to the general procedure using 2-ethylhexyl-1-amine (9.9 mL, 61 mmol) as an amine source. The crude product was purified on CombiFlash® $R_f$ automated flash chromatography system using normal phase silica gel as a stationary phase and gradient 0-40% MeOH in $CH_2Cl_2$ as an eluent system ($R_f$=0.8, 10% MeOH/$CH_2Cl_2$) to yield light brown oil (10.2 g, 99/a). $^1$H NMR (400 MHz, $CDCl_3$) δ 6.36 (br s, 2H), 4.04 (s, 4H), 3.28-3.24 (m, 4H), 1.47-1.45 (m, 2H), 1.34-1.28 (m, 16H), 0.91-0.88 (m, 12H).

2,2'-oxybis(N-(5,9-dimethyldecyl)acetamide) SI-1b was synthesized according to the general procedure using 5,9-dimethyldecan-1-amine (12.5 mL, 54 mmol) as an amine source. The crude product was purified on CombiFlash® $R_f$ automated flash chromatography system using normal phase silica gel as a stationary phase and gradient 0-40% MeOH in $CH_2Cl_2$ as an eluent system ($R_f$=0.5, 5% MeOH/$CH_2Cl_2$) to yield yellow oil (12.0 g, 99%). $^1$H NMR (400 MHz, CDCl3) δ 6.41 (br s, 2H), 4.04 (s, 4H), 3.33-3.28 (m, 4H), 1.54-1.48 (m, 6H), 1.37-1.20 (m, 14H), 1.15-1.06 (m, 8H), 0.87-0.83 (m, 18H). $^{13}$C NMR (100.66 MHz, CDCl3) 168.6, 71.3, 39.4, 39.3, 37.4, 36.8, 32.8, 30.0, 28.1, 24.9, 24.5, 22.8, 22.7, 19.7. HRMS m/z: $[M+H]^+$, calculated for C28H56N2O3, 469.4369; found 469.4378.

2,2'-oxybis(N-(4-butyldecyl)acetamide) SI-1c was synthesized according to the general procedure using 4-butyldecylamine (1.71 g, 8 mmol) as an amine source. The crude product was purified on CombiFlash® $R_f$ automated flash chromatography system using normal phase silica gel as a stationary phase and gradient 0-40% MeOH in $CH_2Cl_2$ as an eluent system ($R_f$=0.4, 5% MeOH/$CH_2Cl_2$) to yield transparent oil (1.98 g, 99%). $^1$H NMR (400 MHz, $CDCl_3$) 6.40 (br s, 2H), 4.04 (s, 4H), 3.31-3.26 (m, 4H), 1.53-1.49 (m, 2H), 1.25-1.23 (m, 40H), 0.90-0.87 (m, 12H). $^{13}$C NMR (100.66 MHz, $CDCl_3$) 168.4, 71.4, 39.7, 37.3, 33.7, 33.3, 32.1, 30.9, 29.9, 29.0, 27.0, 26.8, 23.3, 22.9, 14.3, 14.3. HRMS m/z: $[M+H]^+$, calculated for C32H64N2O3, 525.4995; found 525.5009.

2,2'-oxybis(N-octylacetamide) SI-1d was synthesized according to the general procedure using octylamine (13.2 mL, 82 mmol) as an amine source. After completion of the reaction, DI water (3×100 mL) was added, the organic layer was separated and washed with saturated NaCl solution, then dried over $MgSO_4$, filtered and concentrated under reduced pressure. Afterwards, $Et_2O$ (100 mL) was added to the crude product and the formed crystals were filtrated off. The product was obtained as a white crystalline powder (11.7 g, 84%). $^1$H NMR (400 MHz, $CDCl_3$) 6.41 (br s, 2H), 4.04 (s, 4H), 3.38-3.28 (m, 4H), 1.55-1.51 (m, 4H), 1.30-1.27 (m, 20H), 0.88 (t, J=6.8 Hz, 6H).

General procedure for the synthesis of N,N'-disubstituted 2,2'-oxybisacetamide ligands 4-8, 12, 14, 15: Compounds (ligands) 4-8, 12, 14, 15 were prepared following this procedure. To a mixture of NaH (2.2 equiv.) in anhydrous THF (0.3 M) was added N,N'-monosubstituted 2,2'-oxybisacetamide SI-1a-d dissolved in anhydrous THF (0.3 M) under inert atmosphere. The reaction mixture was stirred at room temperature for 15 minutes, before the addition alkyl iodide (3 equiv.) and further stirred at room temperature for ~12 hours. To the reaction mixture EtOH was added to neutralize excess NaH. The reaction mixture was concentrated under reduced pressure to yield crude product. See below for further details on purification.

2,2'-oxybis(N-(2-ethylhexyl)-N-methylacetamide) 4 was synthesized according to the general procedure using 2,2'-oxybis(N-(2-ethylhexyl)acetamide) SI-1a (4.35 g, 12 mmol) and methyl iodide (2.24 mL, 36 mmol) as an alkyl iodide source. Product was purified on CombiFlash® $R_f$ automated flash chromatography system using normal phase silica gel as a stationary phase and gradient 0-30% MeOH in $CH_2Cl_2$ as an eluent system ($R_f$=0.7, 10% MeOH/$CH_2Cl_2$) to yield transparent oil (4.21 g, 91%). $^1$H NMR (400 MHz, $CDCl_3$) 4.32 (s, 4H), 3.34-3.30 (m, 1H), 3.26-3.24 (m, 1H), 3.12-3.10 (m, 2H), 2.93-2.89 (m, 6H), 1.64-1.58 (m, 2H), 1.26-1.22 (m, 16H), 0.88-0.84 (m, 12H). $^{13}$C NMR (100.66 MHz, $CDCl_3$) 169.4, 169.3, 169.1, 169.0, 69.6, 69.4, 69.1, 68.9, 52.8, 51.3, 37.9, 37.0, 34.5, 33.5, 30.4, 30.4, 28.8, 28.7, 23.6, 23.1, 23.0, 14.1, 14.1, 10.9, 10.6. HRMS m/z: $[M+H]^+$, calculated for C22H44N2O3, 385.3430; found 385.3435.

2,2'-oxybis(N-(4-butyldecyl)-N-methylacetamide) 5 was synthesized according to the general procedure using 2,2'-oxybis(N-(4-butyldecyl)acetamide) SI-1c (2.03 g, 3.9 mmol) and methyl iodide (0.75 mL, 12 mmol) as an alkyl iodide source. The product was purified on CombiFlash® $R_f$ automated flash chromatography system using normal phase silica gel as a stationary phase and gradient 0-40% MeOH in $CH_2Cl_2$ as an eluent system ($R_f$=0.4, 5% MeOH/$CH_2Cl_2$) to yield transparent oil (1.9 g, 90%). $^1$H NMR (400 MHz, $CDCl_3$) 4.32-4.30 (m, 4H), 3.32 (t, J=7.4 Hz, 2H), 3.21 (t, J=7.5 Hz, 2H), 2.96 (s, 3H), 2.92 (s, 3H), 1.53-1.48 (m, 2H), 1.24-1.22 (m, 40H), 0.90-0.86 (m, 12H). $^{13}$C NMR (100.66 MHz, $CDCl_3$) 169.0, 168.9, 168.8, 168.7, 69.7, 69.6, 69.3, 69.2, 49.5, 48.4, 37.4, 33.7, 33.3, 32.1, 32.0, 29.9, 29.9, 29.02, 29.0, 26.8, 26.7, 23.2, 22.8, 14.3, 14.3. HRMS m/z: $[M+H]^+$, calculated for C34H68N2O3, 553.5308; found 553.5318.

2,2'-oxybis(N-(5,9-dimethyldecyl)-N-methylacetamide 6 was synthesized according to the general procedure using 2,2'-oxybis(N-(5,9-dimethyldecyl)acetamide) SI-1b (4.0 g, 9 mmol) and $CH_3I$ (1.7 mL, 27 mmol) as an alkyl iodide source. The product was purified on CombiFlash® $R_f$ automated flash chromatography system using normal phase silica gel as a stationary phase and gradient 0-30% MeOH in $CH_2Cl_2$ as an eluent system ($R_f$=0.7, 10% MeOH/$CH_2Cl_2$) to yield transparent oil (3.6 g, 81%). $^1$H NMR (400 MHz, $CDCl_3$) 4.33-4.31 (m, 4H), 3.36-3.32 (t, J=3.5 Hz, 2H), 3.24-3.20 (t, J=3.5, 2H), 2.96 (s, 3H), 2.91 (s, 3H), 1.54-1.48 (m, 6H), 1.35-1.20 (m, 14H), 1.13-1.07 (m, 8H), 0.87-0.82 (m, 18H). $^{13}$C NMR (100.66 MHz, $CDCl_3$) 169.0, 168.9, 169.8, 168.7, 69.7, 69.6, 69.3, 69.2, 49.2, 48.2, 39.5, 37.4, 37.3, 37.0, 36.9, 34.4, 33.4, 32.9, 28.8, 28.1, 27.6, 24.9, 24.5, 24.3, 22.9, 22.8, 19.8, 19.7. HRMS m/z: $[M+H]^+$, calculated for C30H60N2O3, 497.4682; found 497.4691.

2,2'-oxybis(N-ethyl-N-octylacetamide) 7 was synthesized according to the general procedure using 2,2'-oxybis(N-octylacetamide) SI-1d (4.35 g, 12 mmol) and ethyl iodide (1.36 mL, 17 mmol) as an alkyl iodide source. Product was purified on CombiFlash® Rf automated flash chromatography system using normal phase silica gel as a stationary phase and gradient 0-40% MeOH in $CH_2Cl_2$ as an eluent system ($R_f$=0.8, 60% EtOAc/Hexanes) to yield transparent oil (2.32 g, 85%). $^1$H NMR (400 MHz, $CDCl_3$) 4.31 (s, 4H), 3.39-3.34 (m, 2H), 3.29 (m, 4H), 3.20-3.16 (m, 2H), 1.52 (s, 4H), 1.27 (s, 20H), 1.17-1.12 (m, 6H), 0.87 (s, 6H). $^{13}$C NMR (100.66 MHz, $CDCl_3$) 168.4, 69.5, 69.5, 69.3, 69.3, 46.8, 45.5, 45.5, 41.6, 40.7, 31.9, 31.9, 29.5, 29.5, 29.4, 29.3, 22.8, 22.7, 14.3, 14.2, 13.0. HRMS m/z: $[M+H]^+$, calculated for C24H48N2O3, 413.3743; found 413.3752.

2,2'-oxybis(N-octyl-N-propylacetamide) 8 was synthesized according to the general procedure using 2,2'-oxybis(N-octylacetamide) SI-1d (2 g, 5.6 mmol) and propyl iodide (1.67 mL, 17 mmol) as an alkyl iodide source. Product was purified on CombiFlash® $R_f$ automated flash chromatography system using normal phase silica gel as a stationary phase and gradient 0-40% MeOH in $CH_2Cl_2$ as an eluent system ($R_f$=0.8, 60% EtOAc/Hexanes) to yield transparent oil (2.35 g, 95%). $^1$H NMR (400 MHz, $CDCl_3$) 4.31 (s, 4H), 3.31-3.25 (m, 4H), 3.18-3.16 (m, 4H), 1.53 (m, 8H), 1.26 (s, 20H), 0.88 (s, 12H). $^{13}$C NMR (100.66 MHz, $CDCl_3$) 168.8, 168.8, 69.3, 69.2, 48.6, 47.5, 47.1, 45.9, 31.9, 31.9, 29.5, 29.5, 29.4, 29.3, 27.7, 27.0, 22.8, 22.8, 22.2, 20.9, 14.2, 11.5, 11.3. HRMS m/z: $[M+H]^+$, calculated for C26H52N2O3, 441.4056; found 441.4067.

Detailed Synthesis for Compounds 9, 10, and 13

The following general synthetic scheme was used:

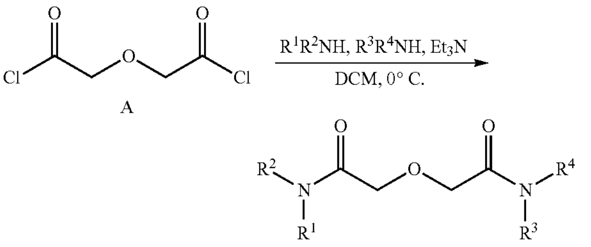

9, 10, 13

General procedure for the synthesis of N,N'-disubstituted 2,2'-oxybisacetamide ligands 9-10: Compounds 9, 10 were prepared following this procedure. To a mixture of $R^1R^2NH$ (1 equiv.) and $R^3R^4NH$ (1 equiv.) in THF (0.3 M) was added $Et_3N$ (2.1 equiv.). The reaction mixture was cooled in an ice-water bath prior to slow addition of 2,2-oxydiacetyl chloride A (1 equiv.) then stirred at room temperature for 2 hours. The solvent was evaporated under reduced pressure. To the crude material, $Et_2O$ (~0.3 M) was added, the precipitate was removed by filtration through a short Celite® plug and rinsed with $Et_2O$ (2×). The filtrate was concentrated under reduced pressure to yield crude product. See below for further details on purification.

2-(2-(dimethylamino)-2-oxoethoxy)-N,N-dioctylacetamide 9 was synthesized according to the general procedure using 2 M dimethylamine in THF (6.0 mL, 12 mmol) and dioctylamine (3.6 mL, 12 mmol) as secondary amine sources. The product was purified on CombiFlash® $R_f$ automated flash chromatography system using normal phase silica gel as a stationary phase and gradient 0-100% EtOAC in hexanes as an eluent system ($R_f$=0.4, 80% EtOAc/Hexanes) to yield transparent oil (1.68 g, 39%). $^1$H NMR (400 MHz, $CDCl_3$) 4.32 (s, 2H), 4.29 (s, 2H), 3.32-3.26 (m, 2H), 3.20-3.13 (m, 2H), 3.01 (s, 3H), 2.95 (s, 3H), 1.52 (m, 2H), 1.26 (m, 20H), 0.90-0.85 (m, 6H).

2-(2-(dioctylamino)-2-oxoethoxy)-N-methyl-N-octylacetamide 10 was synthesized according to the general procedure using N-methyl-N-octylamine (0.6 mL, 3.3 mmol) and dioctylamine (1.0 mL, 3.3 mmol) as secondary amine sources. The product was purified on CombiFlash® $R_f$ automated flash chromatography system using normal phase silica gel as a stationary phase and gradient 0-100% EtOAC in hexanes as an eluent system ($R_f$=0.2, 20% MeOH/$CH_2Cl_2$) to yield transparent oil (0.72 g, 45%). $^1$H NMR (400 MHz, $CDCl_3$) 4.32-4.29 (m, 4H), 3.34-3.26 (m, 6H), 2.96-2.91 (m, 3H), 1.52 (s, 6H), 1.27 (s, 30H), 0.87 (br s, 9H). $^{13}$C NMR (100.66 MHz, $CDCl_3$) 169.0, 168.9, 168.8, 168.6, 69.7, 69.3, 69.2, 49.2, 48.1, 47.1, 46.0, 46.0, 31.9, 31.9, 29.5, 29.5, 29.5, 29.4, 29.4, 29.3, 27.2, 27.0.

Detailed Synthesis for Compound 11

The following general synthetic scheme was used:

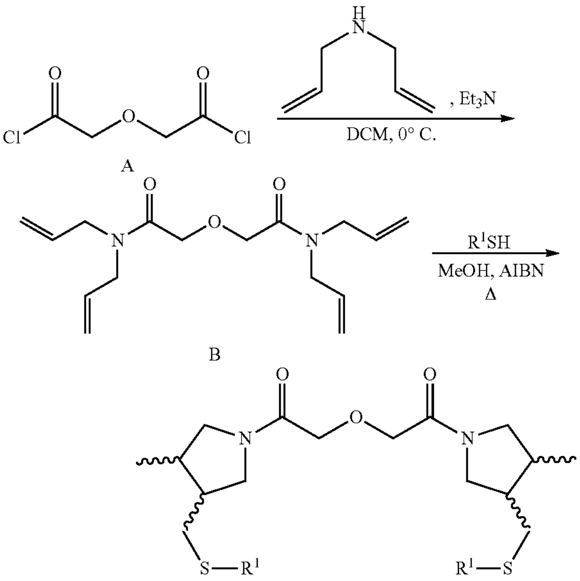

11

2,2'-oxybis(N,N-divinylacetamide) B was synthesized according to the following procedure. To a mixture of diallylamine (32.7 g, 128 mmol, 2.2 equiv.) in THF (0.3 M) was added $Et_3N$ (2.1 equiv.). The reaction mixture was cooled in an ice-water bath prior to slow addition of 2,2-oxydiacetyl chloride A (1 equiv.) then stirred at room temperature for 2 hours. The solvent was evaporated under reduced pressure. To the crude material, $Et_2O$ (~0.3 M) was added, the precipitate was removed by filtration through a short Celite® plug and rinsed with $Et_2O$ (2×). The filtrate was concentrated under reduced pressure to yield crude product (23.6 g) that was used in the next step without further purification. $^1$H NMR (400 MHz, $CDCl_3$) 5.80-5.70 (m, 4H), 5.21-5.12 (m, 8H), 4.30 (s, 4H), 3.99 (d, J=6.0 Hz, 4H), 3.89 (d, J=5 Hz, 4H).

2,2'-oxybis(1-(3-methyl-4-(((2-methylundecan-2-yl)thio)methyl)pyrrolidin-1-yl)ethanone) 11 was synthesized as follows: To a mixture of 2,2'-oxybis(N,N-divinylacetamide) B (1 equiv.) and 1,1-dimethyldecanethiol (3.0 equiv., 71 mL, 301 mmol) in MeOH (0.3 M) was added AIBN (15 mol %). The inert gas was bubbled through the reaction mixture for 30 minutes before heating it at 66° C. for 12 hours. The solvent was evaporated to yield crude product. The product was purified by column chromatography using normal phase silica gel as a stationary phase and gradient 0-50% MeOH in $CH_2Cl_2$ as an eluent system to yield orange oil (90.4 g, 95%). $^1$H NMR (400 MHz, $CDCl_3$) 4.23-4.20 (m, 4H), 3.89-3.78 (m, 1H), 3.70-3.65 (m, 1H), 3.52 (m, 2H), 3.33-3.04 (m, 2H), 2.99-2.95 (m, 1H), 2.70-2.61 (m, 1H), 2.50-2.25 (m, 6H), 2.05-1.82 (m, 4H), 1.58-1.06 (m, 28H), 0.93-0.80 (m, 26H). $^{13}$C NMR (100.66 MHz, $CDCl_3$) 168.0, 167.9, 167.6, 167.4, 69.9, 69.8, 69.7, 69.5, 69.4, 69.3, 53.5, 53.0, 52.8, 51.5, 51.0, 49.4, 49.0, 46.3, 42.4, 40.2, 39.1, 37.0, 35.5, 33.4, 29.5, 29.1, 28.7, 25.8, 23.5, 22.8, 16.3, 14.7, 14.3, 13.3, 13.1, 12.3, 11.6, 9.0, 8.8, 8.5. HRMS m/z: [M+H], calculated for C40H76N2O3S2, 697.5376; found 697.5380.

2,2'-oxybis(N-dodecyl-N-octylacetamide) 12 was synthesized according to the general procedure using 2,2'-oxybis (N-octylacetamide) SI-1d (12.25 g, 34 mmol) and dodecyl iodide (30.22 g, 102 mmol) as an alkyl iodide source. The product was purified on CombiFlash® $R_f$ automated flash chromatography system using normal phase silica gel as a stationary phase and gradient 0-40% MeOH in $CH_2Cl_2$ as an eluent system ($R_f$=0.8, 10% MeOH/$CH_2Cl_2$) to yield light brown oil (21.7 g, 92%). $^1$H NMR (400 MHz, $CDCl_3$) 4.33 (s, 4H), 3.31-3.27 (m, 4H), 3.19-3.15 (m, 4H), 1.54-1.48 (m, 8H), 1.25 (m, 56H), 0.89-0.86 (m, 12H). $^{13}$C NMR (100.66 MHz, $CDCl_3$) 168.8, 69.2, 47.1, 46.0, 32.1, 32.0, 31.9, 29.8, 29.7, 29.5, 29.5, 29.5, 29.1, 27.7, 27.2, 27.0, 22.8, 22.8, 22.8, 14.3, 14.2. HRMS m/z: $[M+Na]^-$, calculated for C44H88N2O3, 715.6687; found 715.6693.

Detailed Synthesis for Compound SI-3

The following general synthetic scheme was used:

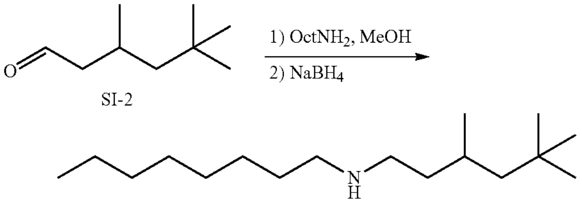

SI-2

SI-3

N-(3,5,5-trimethylhexyl)octan-1-amine (SI-3). To a mixture of 3,5,5-trimethylhexanal SI-2 (25 mL, 144 mmol) in MeOH (290 mL) was added octylamine (23.7 mL, 144 mmol). The reaction mixture was stirred at room temperature for 12 hours. Afterwards, $NaBH_4$ (6.5 g, 172 mmol) was added in small portions and reaction mixture stirred at room temperature for 2 hours. After the removal of reaction solvent on a rotary evaporator, 400 mL of $Et_2O$ were added. The suspension was filtrated through a short silica gel-Celite® plug and washed with $Et_2O$ (2×). The filtrate was concentrated under reduced pressure to yield product (32.7 g, 89%) which was used in the next step without further purification. $^1$H NMR (400 MHz, $CDCl_3$) 2.58 (t, J=7.3 Hz, 4H), 2.38 (m, 1H), 1.53-1.42 (m, 2H), 1.35-1.20 (m, 14H), 1.07-1.03 (m, 1H), 0.93-0.86 (m, 15H).

2,2'-oxybis(N-octyl-N-(3,5,5-trimethylhexyl)acetamide) 13 was synthesized according to the general procedure using N-(3,5,5-trimethylhexyl)octan-1-amine 7 (21.8 mL, 176 mmol, 2.1 equiv.) as a secondary amine source. The product was purified on CombiFlash® $R_f$ automated flash chromatography system using normal phase silica gel as a stationary phase and gradient 10-60% EtOAc in hexanes as an eluent system ($R_f$=0.6, 60% EtOAc/Hex) to yield transparent oil (25.0 g, 71%). $^1$H NMR (400 MHz, $CDCl_3$) 4.29 (s, 4H), 3.28-3.25 (m, 4H), 3.17-3.14 (m, 4H), 1.52-1.49 (m, 24H), 1.09-1.05 (m, 2H), 0.95-0.86 (m, 30H). $^{13}$C NMR (100.66 MHz, CDCl3) 168.5, 168.5, 69.2, 51.3, 51.2, 47.0, 46.0, 45.5, 44.3, 38.5, 36.9, 31.9, 21.2, 20.1, 20.1, 29.4, 29.3, 27.7, 22.8, 22.7, 14.2. HRMS m/z: $[M+H]^+$, calculated for C38H77N2O3, 609.5934; found 609.5946.

2,2'-oxybis(N-(4-butyldecyl)-N-octylacetamide) 14 was synthesized according to the general procedure using 2,2'-oxybis(N-(4-butyldecyl)acetamide) SI-1c (19.03 g, 36 mmol) and octyl iodide (19.5 mL, 108 mmol) as an alkyl iodide source. The product was purified on CombiFlash® $R_f$ automated flash chromatography system using normal phase silica gel as a stationary phase and gradient 0-40% MeOH in $CH_2Cl_2$ as an eluent system ($R_f$=0.8, 10% MeOH/$CH_2Cl_2$) to yield light brown oil (25.6 g, 95%). $^1$H NMR (400 MHz, $CDCl_3$) 4.37 (s, 4H), 3.31-3.25 (m, 4H), 3.19-3.16 (m, 4H), 1.52-1.50 (m, 8H), 1.27-1.22 (m, 58H), 0.90-0.86 (m, 18H). HRMS m/z: $[M+H]^+$, calculated for C48H96N2O3, 749.7494; found 749.7491.

2,2'-oxybis(N-(5,9-dimethyldecyl)-N-octylacetamide) 15 was synthesized according to the general procedure using 2,2'-oxybis(N-(5,9-dimethyldecyl)acetamide) SI-1b (20.17 g, 43 mmol) and octyl iodide (23.3 mL, 129 mmol) as an alkyl iodide source. The product was purified on CombiFlash® $R_f$ automated flash chromatography system using normal phase silica gel as a stationary phase and gradient 0-40% MeOH in $CH_2C_2$ as an eluent system ($R_f$=0.8, 10% MeOH/$CH_2Cl_2$) to yield light brown oil (28.6 g, 96%). $^1$H NMR (400 MHz, $CDCl_3$) 4.32 (s, 4H), 3.31-3.27 (m, 4H), 3.19-3.16 (m, 4H), 1.54-1.49 (m, 8H), 1.35-1.10 (m, 44H), 0.87-0.82 (m, 24H). $^{13}$C NMR (100.66 MHz, $CDCl_3$) 168.9, 69.2, 47.2, 46.1, 46.1, 39.5, 37.5, 37.4, 36.9, 36.9, 32.9, 31.9, 31.9, 29.5, 29.5, 29.4, 29.0, 28.1, 28.0, 27.7, 27.2, 27.0, 24.9, 24.7, 24.5, 22.9, 22.8, 22.8, 19.8, 19.7, 14.2. HRMS m/z: $[M+H]^+$, calculated for C44H88N2O3, 693.6868; found 693.6870.

Detailed Synthesis for Compound SI-5 and SI-6

The following general synthetic scheme was used:

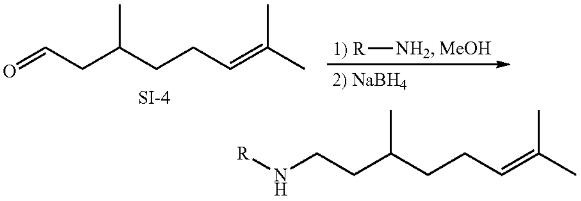

SI-4

SI-5 R = n-hexyl
SI-6 R = n-dodecyl

N-hexyl-3,7-dimethyloct-6-en-1-amine (SI-5) and N-(3,7-dimethyloct-6-en-1-yl)dodecan-1-amine (SI-6). To a mixture of Citronellal SI-4 (90 mL, 0.5 mol) in MeOH (950 mL) was added either n-hexylamine (66 mL, 0.5 mol) or n-dodecylamine (92.7 g, 0.5 mol). The reaction mixture was stirred at room temperature for 12 hours. Afterwards, $NaBH_4$ (22.7 g, 0.6 mol) was added in small portions and reaction mixture stirred at room temperature for 2 hours. After the removal of reaction solvent on a rotary evaporator, 400 mL of $Et_2O$ were added. The suspension was filtrated through a short silica gel-Celite® plug and washed with $Et_2O$ (2×). The filtrate was concentrated under reduced pressure to yield product which was used in the next step without further purification.

2,2'-oxybis(N-(3,7-dimethyloct-6-en-1-yl)-N-hexylacetamide) SI-7 and 2,2'-oxybis(N-(3,7-dimethyloct-6-en-1-yl)-N-dodecylacetamide) SI-8 were synthesized according to the general procedure using N-hexyl-3,7-dimethyloct-6-en-1-amine SI-5 (103 g, 0.43 mol, 2.1 equiv.) and N-(3,7-dimethyloct-6-en-1-yl)dodecan-1-amine SI-6 (10 g, 0.031 mol, 2.1 equiv.) as a secondary amine source, respectively. Each product was purified on CombiFlash® $R_f$ automated flash chromatography system using normal phase silica gel as a stationary phase and gradient 10-60% EtOAc in hexanes as an eluent system ($R_f$=0.6, 60% EtOAc/Hex) to yield transparent oil (SI-7, 67.3 g, 60% and SI-8, 6.6 g, 57%).

2,2'-oxybis(N-(3,7-dimethyloctyl)-N-hexylacetamide) 16 and 2,2'-oxybis(N-(3,7-dimethyloctyl)-N-dodecylacetamide) 17 were synthesized via hydrogenation of 2,2'-oxybis(N-(3,7-dimethyloct-6-en-1-yl)-N-hexylacetamide) SI-7 and 2,2'-oxybis(N-(3,7-dimethyloct-6-en-1-yl)-N-dodecylacetamide) SI-8 using 10% Pd/C (2.4 g/0.1 mol of SI-7 or SI-8) in MeOH (0.2 M) and $H_2$ (1 atm, balloon). Each reaction mixture was filtrated through a short Celite® plug and washed with MeOH. The filtrate was concentrated under reduced pressure to yield product as light-yellow oil (99% yield). Compound 16: $^1$H NMR (400 MHz, $CDCl_3$) 4.30 (s, 4H), 3.39-3.03 (m, 8H), 1.60-1.44 (m, 8H), 1.37-1.17 (m, 22H), 1.17-1.04 (m, 6H), 0.95-0.75 (m, 24H). Compound 17: $^1$H NMR (400 MHz, $CDCl_3$) 4.29 (s, 4H), 3.39-3.09 (m, 8H), 1.59-1.45 (m, 8H), 1.36-1.18 (m, 46H), 1.17-1.07 (m, 6H), 0.96-0.78 (m, 24H).

Detailed Synthesis for Compound 18

The following general synthetic scheme was used:

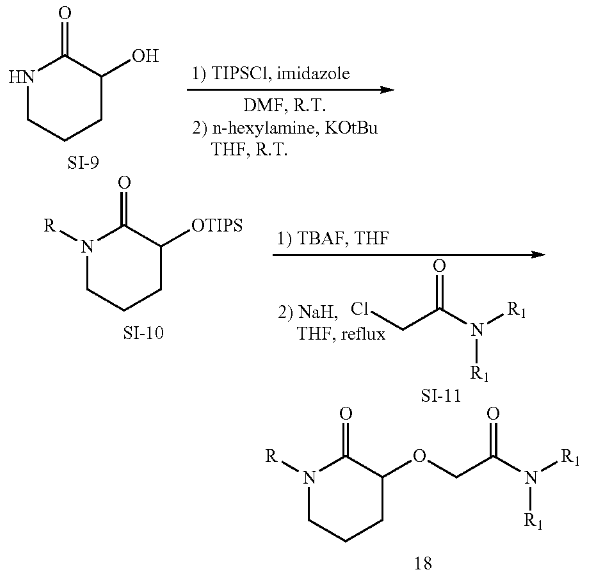

SI-9

SI-10

SI-11

18

1-hexyl-3-((triisopropylsilyl)oxy)piperidin-2-one (SI-10). 3-hydroxypiperidin-2-one SI-9 (2.5 g, 0.02 mol) and imidazole (1.05 equiv) were dissolved in anhydrous DMF (0.2 M). To this solution was then added TIPS-Cl (1.05 equiv) and the reaction mixture was stirred at room temperature for 12 hours. To the reaction mixture was added water and product was extracted with $E_2O$ (3×). The combined organic phase was washed with brine, dried over $MgSO_4$, filtered, and solvent removed under reduced pressure. The product was used in the next step without further purification. To the ice-cold solution of the TIPS protected product (5.9 g, 0.02 mol) in anhydrous THF (0.2 M) was added tBuOK (2.68 g, 0.02 mol). The reaction mixture was stirred for 30 min before the addition of n-hexyl iodide. Afterwards, the reaction mixture was stirred for 12 hours at room temperature. To the reaction mixture was added water and product was extracted with $E_2O$ (3×). The combined organic phase was washed with brine, dried over $MgSO_4$, filtered, and solvent removed under reduced pressure. The product (SI-10) was used in the next step without further purification.

N,N-didodecyl-2-((1-hexyl-2-oxopiperidin-3-yl)oxy)acetamide (18). To 1-hexyl-3-((triisopropylsilyl)oxy)piperidin-2-one SI-10 (0.02 mol) dissolved in anhydrous THF (0.4 M) was added TBAF (1 M in THF, 1.2 equiv). The reaction mixture was stirred at room temperature for 12 hours. Afterwards, the solvent was removed under reduced pressure and product was purified on CombiFlash® $R_f$ automated flash chromatography system using normal phase silica gel as a stationary phase and gradient 0-80% EtOAc in hexanes as an eluent system to yield light yellow oil (3.9 g, 90%). Next, the round bottom flask was charged with NaH (0.25 g, 6.3 mmol) and anhydrous THF (0.2 M) under inert atmosphere. To the reaction mixture was then added dropwise the above obtained product (1.26 g, 6.3 mmol) dissolved in 5 mL of anhydrous THF. The reaction mixture was stirred at room temperature for 30 minutes. Afterwards, 2-chloro-N,N-didodecylacetamide SI-11 (3.0 g, 6.3 mmol) dissolved in anhydrous THF (5 mL) was added to the reaction mixture. The reaction mixture was heated at 35° C. for 12 hours. To the reaction mixture was added water and product was extracted with $E_2O$ (3×). The combined organic phase was washed with brine, dried over $MgSO_4$, filtered, and solvent removed under reduced pressure. and product was purified on CombiFlash® $R_f$ automated flash chromatography system using normal phase silica gel as a stationary phase and gradient 0-80% EtOAc in hexanes as an eluent system to yield light yellow oil (2.7 g, 73%). $^1$H NMR (400 MHz, $CDCl_3$) 4.73-4.55 (m, 2H), 4.00-3.92 (m, 1H), 3.38-3.05 (m, 8H), 2.24-2.12 (m, 1H), 2.07-1.94 (m, 2H), 1.86-1.65 (m, 3H), 1.60-1.45 (m, 6H), 1.35-1.18 (m, 40H), 0.93-0.83 (m, 9H).

Detailed Synthesis for Compound 20

The following general synthetic scheme was used:

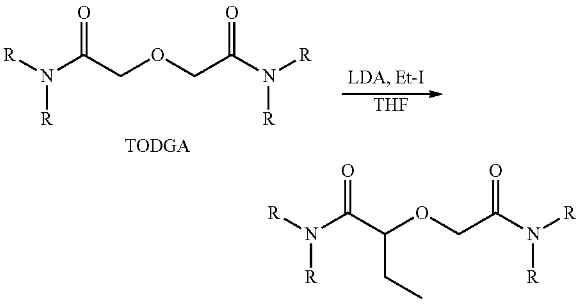

TODGA

20

2-(2-(dioctylamino)-2-oxoethoxy)-N,N-dioctylbutanamide (20). To the solution of TODGA (5.8 g, 10.0 mmol) in anhydrous THF (100 mL) at −90° C. was added dropwise LDA (2 M, 10.5 mmol). The reaction mixture was allowed to warm up to −30° C. and at this temperature ethyl iodide (3.1 g, 20 mmol) was added. The reaction mixture was stirred at room temperature for 12 hours. Afterwards, the solvent was removed under reduced pressure and product was purified on CombiFlash® $R_f$ automated flash chromatography system using normal phase silica gel as a stationary phase and gradient 0-80% EtOAc in hexanes as an eluent system to yield light yellow oil (3.6 g, 59%). $^1$H NMR (400 MHz, $CDCl_3$) 4.36-4.31 (m, 1H), 4.09 (dd, J=167.6, 13.8 Hz, 2H), 3.50-3.38 (m, 1H), 3.38-3.13 (m, 7H), 1.86-1.66 (m, 2H), 1.58-1.44 (m, 8H), 1.36-1.18 (m, 40H), 1.01 (t, J=7.5 Hz, 3H), 0.94-0.82 (m, 12H).

Metal Extraction Experiments

General procedure: A 750 microliter (μL) aqueous phase consisting of 7 mM Ln(III) (0.5 mM of each Ln(III)) in 3 M HCl was contacted with an equal volume of organic phase containing 0.1 M DGA ligands 1-13 in organic solvents that was pre-equilibrated with the 3M HCl. The two phases were contacted at a 1:1 ratio of organic/aqueous by end-over-end rotation in individual 1.8 mL capacity snap-top Eppendorf tubes using a rotating wheel in an air box set at 25.5° C.±0.5° C. Contacts were performed in triplicate with a contact time of 1 hour. Following contacting, the triplicate samples were subjected to centrifugation at 1,811×g for two minutes at 20° C. to separate the phases. Each triplicate was then sub-sampled, with 500 μL aliquots of the aqueous phases transferred to individual polypropylene tubes containing 2.5 mL of 4% HNO3 for analysis using ICP-OES. Two samples of the initial lanthanide solution were also prepared for the analysis, 500 μL were transferred to individual polypropylene tubes containing 2.5 mL of 4% $HNO_3$. The areas found under the observed peaks were used for determining distribution (D) values.

D Values are calculated according to the following equation:

$$D=[M]_{org}/[M]_{aq} \qquad \text{Eq. 1}$$

Separation factors are calculated according to the following equation:

$$SF=D_{Ln1}/D_{Ln2}=X/Y \qquad \text{Eq. 2}$$

The separation of trivalent lanthanides from hydrochloric acid in this study was performed under conditions that are relevant to REE refining. Readily available isoparaffinic hydrocarbon (Isopar L) mixed with 30 vol % of branched aliphatic alcohol (Exxal 13) was used as an oil phase and 3 M hydrochloric acid in water as an aqueous phase. The use of aliphatic alcohol (30 vol %) as a phase modifier prevents third-phase or gel formation. The distribution ratios (D), calculated from competitive metal ion extraction studies, where the concentration of metal ion in the organic phase is divided by its concentration in the aqueous phase, simultaneously provide information on the extraction strength, selectivity, and the point in the series at which these effects are no longer noticeable (the leveling effect). The selectivity of separating two metal ions is expressed as the separation factor, defined as the ratio of one metal to that of another; for example, $SF_{Lu/La}=D_{Lu}/D_{La}$. All experiments were performed in triplicate using ligand 1 as a control for all measurements presented in this work.

Prior to extraction, the prepared organic phases were pre-equilibrated with 3 M HCl solution, i.e., identical solutions as used in extraction, only in the absence of the studied metal. For that, one volume of the organic phase was agitated for 10 minutes with three-fold volume of 3 M HCl, and agitation was repeated two more times. The equilibrated organic phases were contacted with aqueous phases containing 1.2 mmol/L of the stable Eu and activity concentration 3.7E+4 Bq/mL of Eu in 1:1 o:a volume ratio in 1.8 mL capacity snap-top Eppendorf tubes. Extraction was performed via vigorous shaking for 60 minutes at 4500 rpm using a vortex mixer at 25° C., followed by centrifugation at 10000 rpm for 5 minutes. All extractions were performed in duplicate, and values of distribution ratios were determined using Eq. 1, as a ratio of activity concentrations in organic and aqueous phases.

Phases were separated using a fine tipped transfer pipet and each sample was then sub-sampled, with 300 μL aliquots of the organic and aqueous phases transferred to individual polypropylene tubes for gamma counting. The activity concentrations were measured using gamma spectroscopy of 300 μL aliquots of each liquid phase, using a NaI(Tl) scintillation counter (Packard COBRA II). The peaks in gamma-spectrum considered were those between 105-143 keV. The measurement times were set in order to obtain a relative standard deviation of the counting statistics lower than 1%.

FIG. 1 is a graph plotting variation of log D in the extraction of Ln(III), 0.5 mM each, with 0.1 M DGA ligands 1 (TODGA), 2 (TEHDGA), and 3 (DMDODGA) from 3 M HCl media into Isopar L with 30 vol % of Exxal 13 at 25° C. after 1 hour. The dotted horizontal line represents the leveling off point. The nonlinear ascending trend is observed across the Ln(III) series by diglycolamide ligands and may be explained by the increased ion-dipole interactions between the extractant molecules and Ln(III) with smaller ionic radius and the ability of extractant molecules to dehydrate Ln(III) during the separation process. It is known that the hydration energy of Ln(III) ions increases and ionic radius decreases with increasing atomic number. Since the electron density of the oxygen atoms for the DGA ligands is comparable (with exception of ligand 11), the change in Log D versus Ln(III) may be attributed to the conformational changes in DGA molecules due to the presence of N,N'-alkyl substituents of varying size. A minimization of allylic strain (A1,3 strain) between the alkyl substituents on amide nitrogen and amide carbonyl group as well as minimization of eclipsing interactions in alkyl chains is needed to eliminate disfavoring interactions. These disfavoring interactions increase as the alkyl substituents get longer and larger in size and affect the accessibility of Ln(III) ions to complex with oxygen donor atoms in DGA.

The reduction of the steric hinderance around the metal center (DMDODGA<TODGA<TEHDGA) results in a dramatic increase in extraction strength (FIG. 1). The replacement of N,N-n-octyl substituents in 1 with methyl groups (3) results in a large increase in D ratios for all Ln(III), but lower overall selectivity, since even the most poorly extracted La(III) has an increase in D ratio by over an order of magnitude (Table 1 below).

TABLE 1

Dependence of alkyl substituents length, size and branching point on the separation of Ln(III) from 3M HCl using 0.1M Ligand in Isopar L with 30% v/v Exxal 13 at 25° C. BDL: below detection limit.

| Ligand | R | R' | Branching | $D_{La}$ | $D_{Sm}$ | $SF_{Sm/La}$ | $D_{Pr}$ | $D_{Nd}$ | $SF_{Nd/Pr}$ |
|---|---|---|---|---|---|---|---|---|---|
| 1 (TODGA) | n-octyl | n-octyl | — | 0.08 ± 0.47 | 5.99 ± 0.07 | 75 | 0.34 ± 0.15 | 0.85 ± 0.09 | 2.5 |
| 2 (TEHDGA) | 2-ethylhexyl | 2-ethylhexyl | β | 0.04 ± 0.01 | 0.11 ± 0.01 | 3 | 0.07 ± 0.01 | 0.08 ± 0.01 | 1.1 |
| 3 (DMDODGA) | methyl | n-octyl | — | 4.15 ± 0.02 | 259.09 ± 0.17 | 62 | 17.45 ± 0.01 | 48.22 ± 0.05 | 2.8 |
| 4 | methyl | 2-ethylhexyl | β | 0.78 ± 0.04 | 40.89 ± 0.29 | 52 | 4.64 ± 0.06 | 11.65 ± 0.12 | 2.5 |
| 5 | methyl | 4-butyldecyl | δ | 0.14 ± 0.06 | 2.66 ± 0.05 | 19 | 0.34 ± 0.04 | 0.60 ± 0.04 | 1.8 |
| 6 | methyl | 5,9-dimethyldecyl | ε | 0.66 ± 0.04 | 8.37 ± 0.20 | 13 | 1.50 ± 0.06 | 2.66 ± 0.08 | 1.8 |
| 7 | ethyl | n-octyl | — | 0.73 ± 0.04 | 61.94 ± 0.10 | 85 | 4.89 ± 0.05 | 10.35 ± 0.05 | 2.1 |
| 8 | propyl | n-octyl | — | 0.34 ± 0.07 | 38.47 ± 0.10 | 113 | 2.84 ± 0.05 | 5.86 ± 0.05 | 2.1 |
| 9 | N,N'-di(n-octyl) | N,N'-dimethyl | — | 3.69 ± 0.04 | BDL | — | 22.30 ± 0.08 | 70.54 ± 0.16 | 3.2 |
| 10 | N,N'-di(n-octyl) | N-methyl-N'-n-octyl | — | 0.34 ± 0.10 | 23.16 ± 0.08 | 68 | 2.01 ± 0.07 | 3.61 ± 0.07 | 1.8 |
| 11 | — | 2-methyldecan-2-yl | — | 1.93 ± 0.07 | 21.49 ± 0.05 | 11 | 4.65 ± 0.05 | 5.56 ± 0.06 | 1.2 |
| 12 | n-octyl | n-decyl | — | 0.08 ± 0.07 | 11.14 ± 0.04 | 145 | 0.53 ± 0.03 | 1.44 ± 0.05 | 2.7 |
| 13 | n-octyl | 3,5,5-trimethylhexyl | γ | 0.05 ± 0.07 | 1.52 ± 0.02 | 30 | 0.37 ± 0.02 | 0.28 ± 0.03 | 0.8 |
| 14 | n-octyl | 4-butyldecyl | δ | 0.00 ± 0.05 | 0.67 ± 0.09 | 141 | 0.03 ± 0.03 | 0.10 ± 0.04 | 3.1 |
| 15 | n-octyl | 5,9-dimethyldecyl | ε | 0.04 ± 0.03 | 4.21 ± 0.04 | 97 | 0.23 ± 0.02 | 0.58 ± 0.05 | 2.5 |

Notably, nearly quantitative (>97%) extraction of lanthanides is reached starting at Nd(III) using compound 3 (ligand 3) and at Tb(III) when using compound 1 (ligand 1). In the separation systems involving all 15 lanthanides it has herein been shown that the elements may be grouped into four tetrads using a variety of ligands. A similar effect in the ordering of Ln(III) can be seen in FIG. 1 for ligands 1 and 3 through the use of three curved lines for La—Ho series; the effect after Ho(III) is somewhat unclear. Ligand 2 is by far the weakest DGA ligand in the series, even though the inductive effects should favor strong interactions with metal ions, the steric hindrance originated by ethyl substituents at the β position on N,N,N',N'-hexyl substituents effectively shield the metal ion binding site. The replacement of two out of four 2-ethylhexyl substituents in 2 with methyl groups has more considerable effect on ligand 4 performance than does the change of n-octyl substituents in 1 with two methyl groups (ligand 3).

Figure 2A:
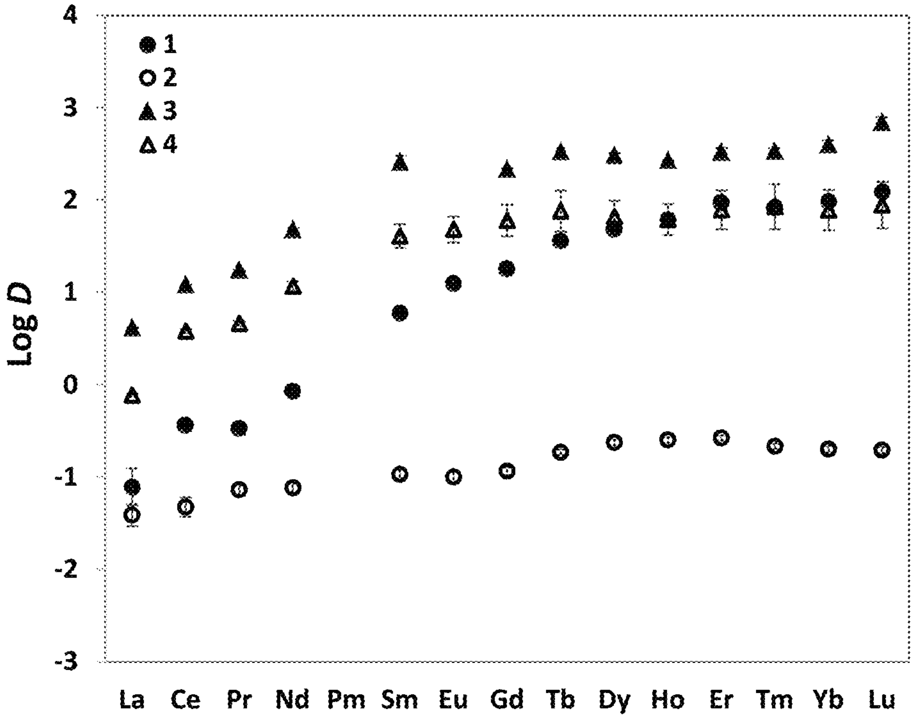
FIGS. 2A-2H are plots showing variation of log D in the extraction of Ln(III), 0.5 mM each, with 0.1 M DGA ligands 1-21 from 3 M HCl media into Isopar L with 30 vol % of Exxal 13 at 25° C. after 1 hour. The log D value for Eu(III) using ligand 3 is missing due to complete extraction, i.e., $Eu^{3+}$ concentration is below the detection limit by ICP-OES. The same is true for Dy(III), Er(III)-Lu(III) using ligand 9.
Figure 2B:
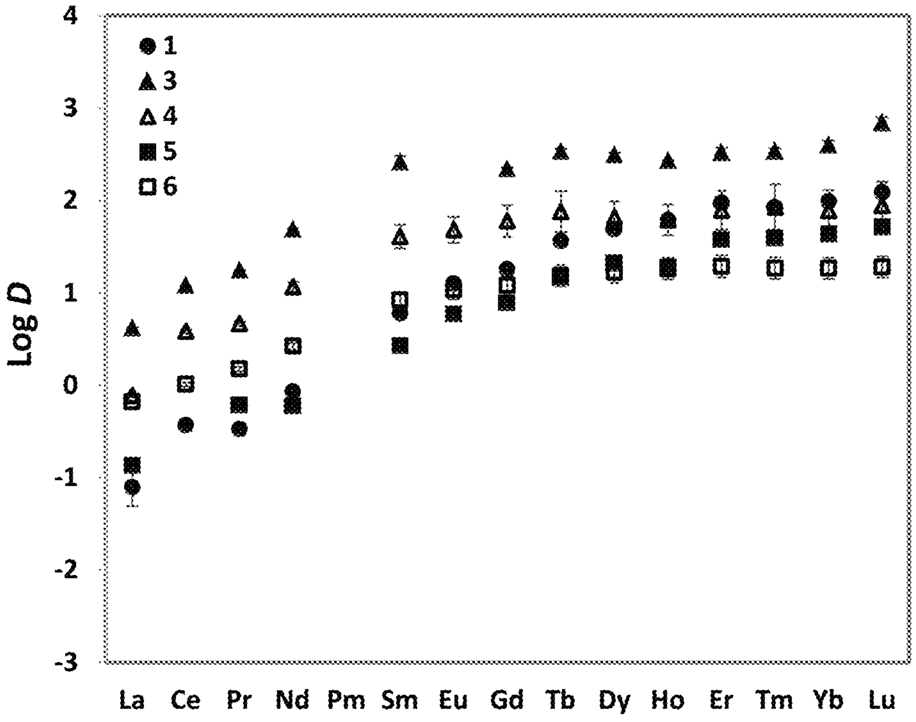
Figure 2C:
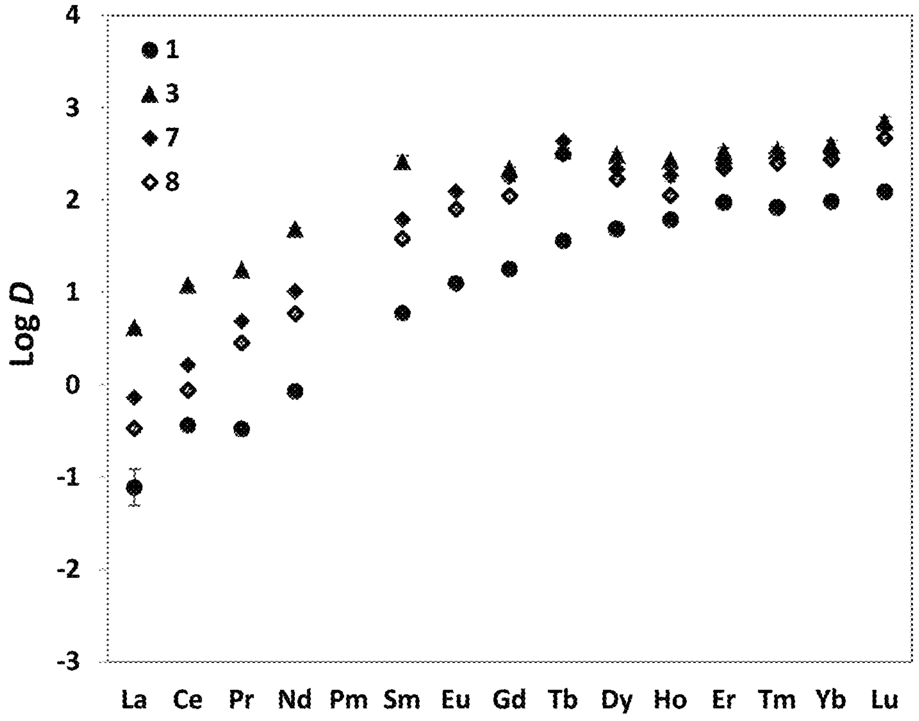
Figure 3A:
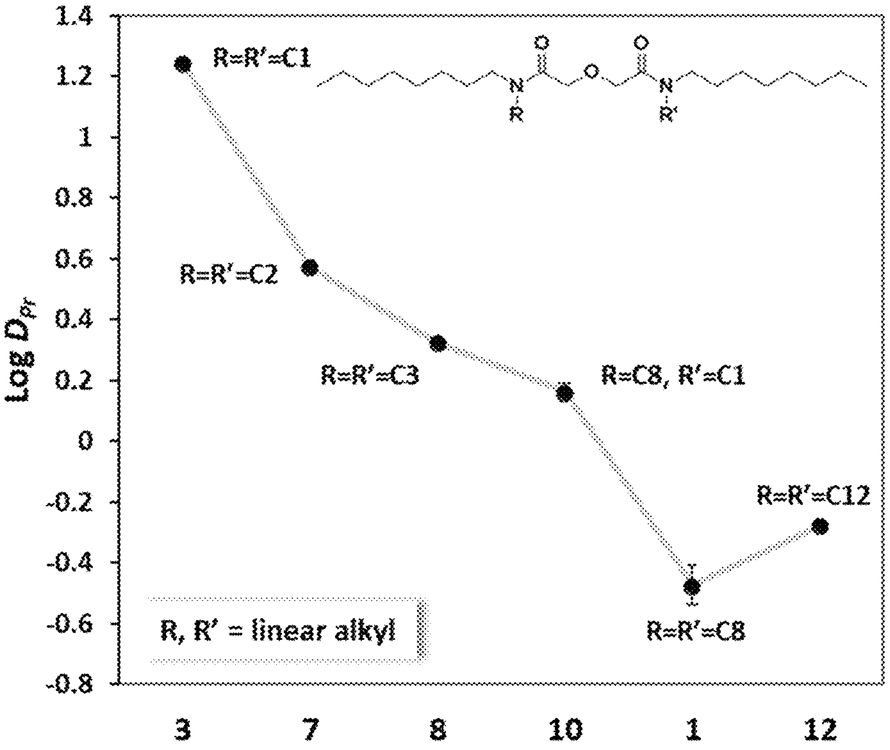
FIGS. 3A-3C are plots showing change in log D for Pr(III) when: a) varying size of two N,N'-linear alkyl substituents in N,N'-di(i-octyl) DGA structure (FIG. 3A); b) varying size of two N,N'-branched alkyl substituents in N,N'-dimethyl-substituted DGA (FIG. 3B); and c) varying size of two N,N'-branched alkyl substituents in N,N'-di(n-octyl)-substituted DGA (FIG. 3C).
Figure 3B:
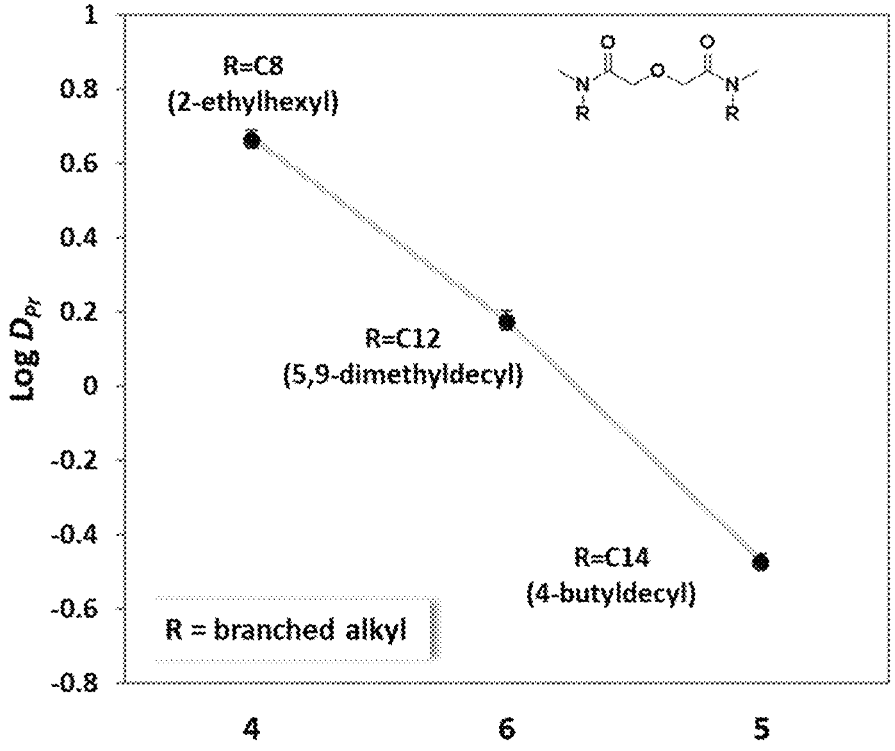

As shown in FIG. 2A, overall, ligand 4 surpasses ligand 1 in terms of extraction strength and shows an increase in D ratio by over two orders of magnitude in comparison to 2. As shown in FIG. 2B, the effects of moving the branching point further away from the binding site in DGA ligand (from β site in 4 to δ in 5, to ε carbon in 6) are pronounced in terms of the extraction strength and selectivity across the Ln(III) series. Ligand 4, which has nearly two times fewer carbons than ligands 5 and 6, performs better in terms of an extraction strength (see FIG. 3B). Ligands 3 and 4 have the same overall carbon count, but due to proximity of the branching sites in ligand 4 to the binding site, the extraction efficiency drops on average 1.3 times (see FIG. 4B). The more structurally similar ligands 5 and 6 show comparable extraction strength of Ln(III), however, their selectivity across the Ln(III) series is notably different. Similar to ligand 4, the extraction curve of ligand 5 levels off starting at Tb(III), whereas ligand 6 shows a steady increase in extraction throughout the series with good selectivity among adjacent lanthanides (e.g., $SF_{Eu/Sm}$=2.2, $SF_{Tb/Gd}$=1.9, $SF_{Er/Ho}$=2.0). A trend in the series of ligands (e.g., for 3, 7, and 8) is that the extraction strength increases with shortening of the alkyl substituent (FIGS. 2C and 3A). Interestingly, this effect is only pronounced in the early lanthanide region (from La to Sm), since all three ligands show comparable D ratios for Eu through Lu.

Figure 2D:
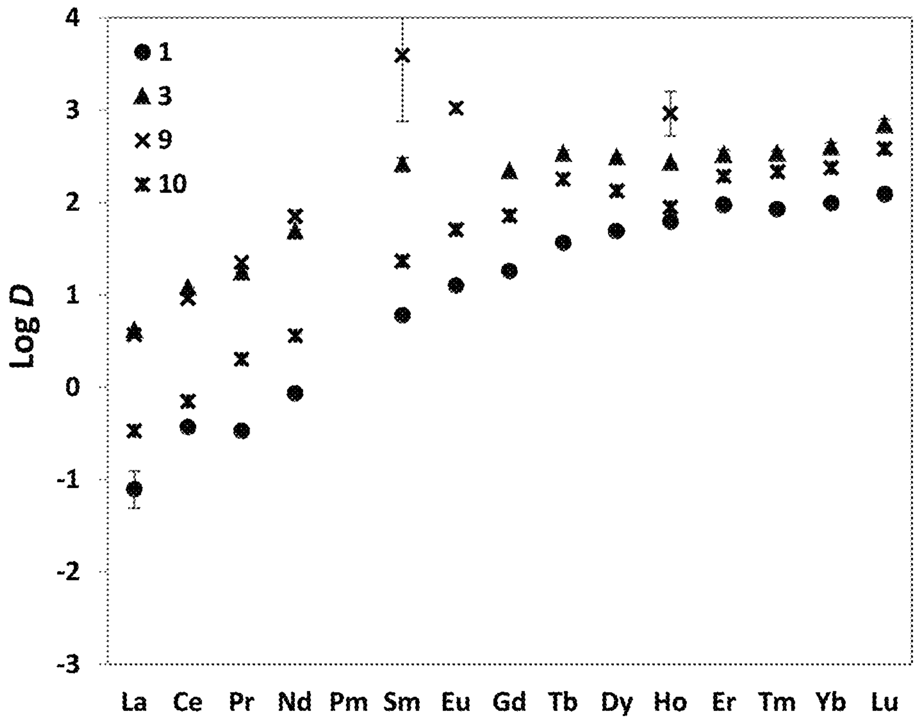
Figure 4A:
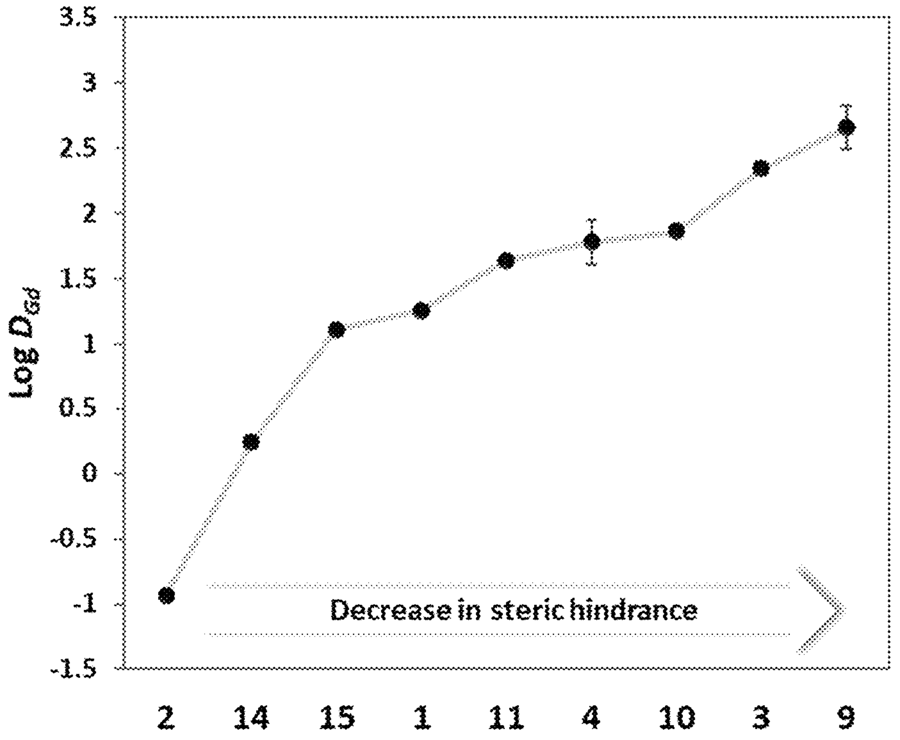
FIGS. 4A-4C are plots showing change in log D for Gd(III) when: a) decreasing steric hindrance around the binding site in DGA (FIG. 4A); b) moving branching site on N,N'-substituent further away from binding site in N,N'-dimethyl-substituted DGA (FIG. 4B); and c) moving branching site on N,N'-substituent further away from binding site in N,N'-di(n-octyl)-substituted DGA (FIG. 4C).
Figure 4B:
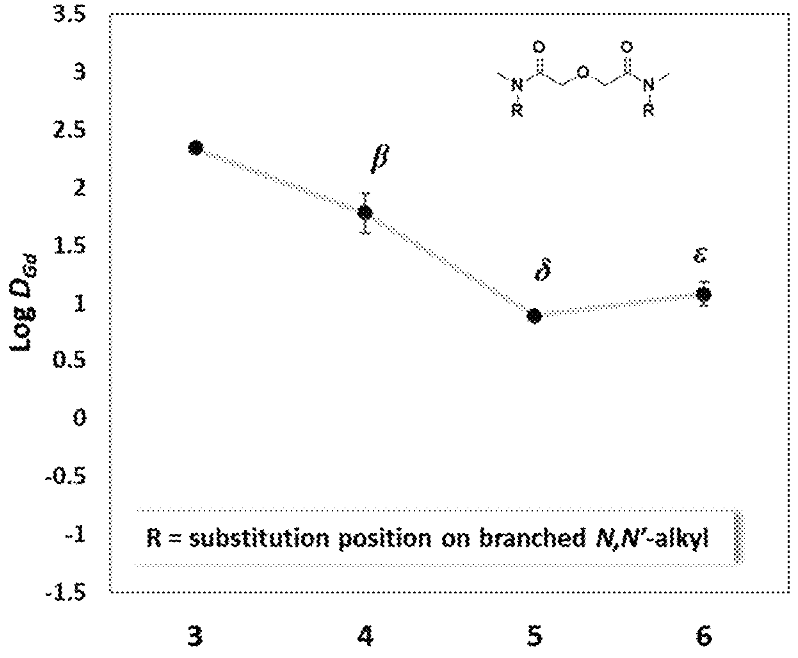

The structural isomer of 3, ligand 9, shows different interfacial properties. Among all ligands, only ligand 9 displayed the third phase formation at 0.1 M ligand concentration when contacted with 3 M HCl solution containing Ln(III). The analysis of aqueous phase after extraction shows steady increase in D ratios from La(III) to Tb(III) and a complete absence of heavier elements (Dy, Er—Lu), which either are held by the ligand in the oil phase or reside as a white precipitate at the oil and water interface. Among all DGA ligands tested, ligand 9 showed the greatest extraction strength, consistent with markedly reduced steric hindrance around the 3-oxygen donor binding site (FIG. 4A). Compound 10, an intermediate ligand between 1, 3 and 9 with only one N-methyl substituent, performs as expected, extracts less of Ln(III) than ligands 3 and 9 but is a stronger extractant than ligand 1 (FIGS. 2D and 4A).

Figure 2E:
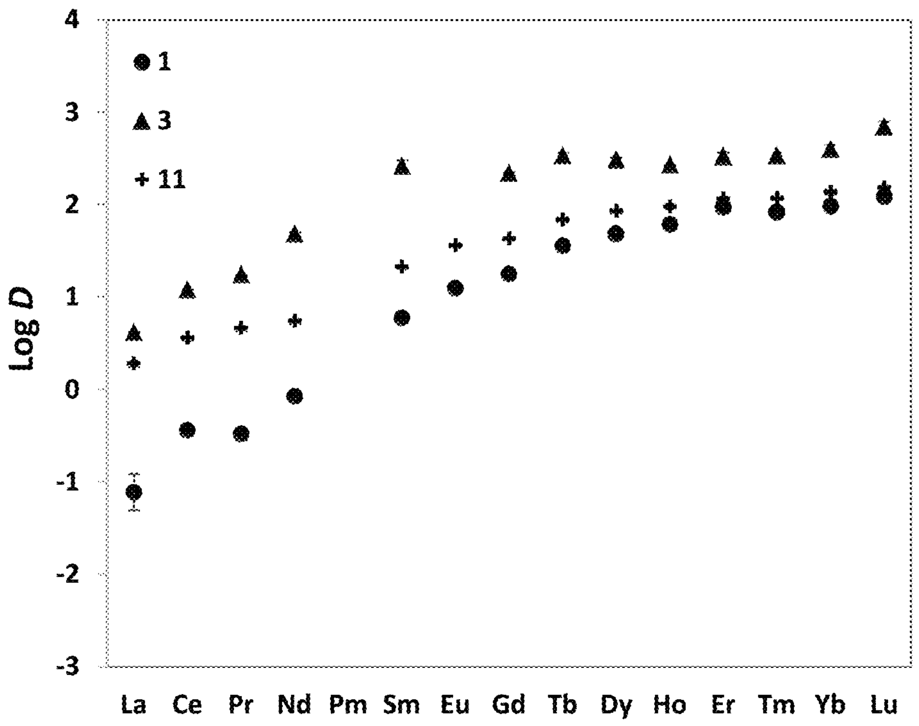
Figure 2F:
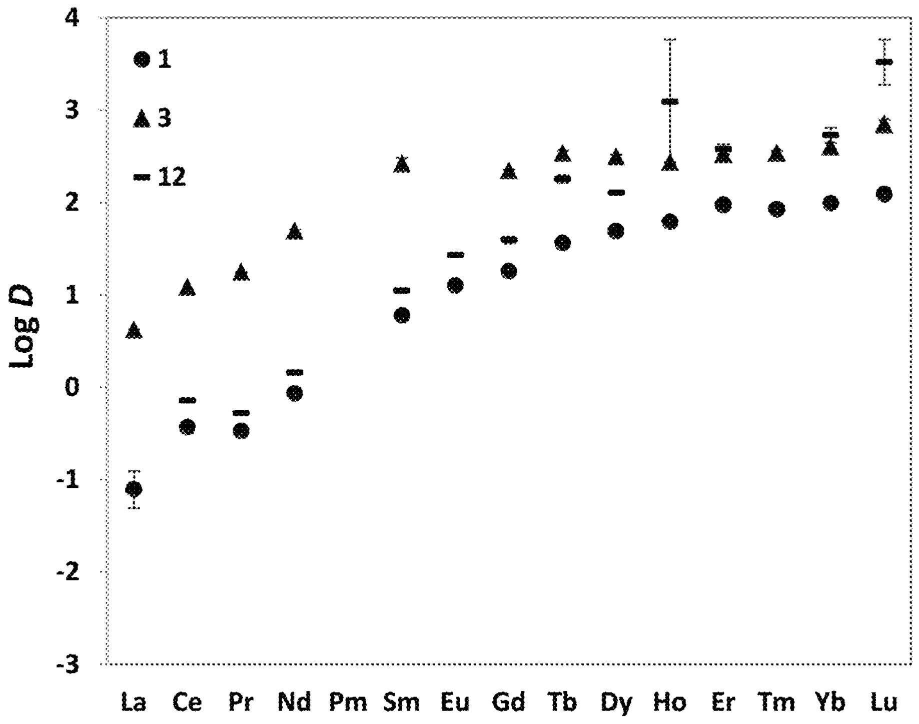

The ligand 11 provides an alternative strategy for reduction of steric hindrance around the metal ion binding site, while maintaining good interfacial properties through the inclusion of long, branched alkyl substituents on pyrrolidines. Based on the results displayed in FIG. 2E and Table 1, the conversion of linear N,N'-alkyl substituents into a 5-membered N-heterocycle results in markedly improved extraction strength of Ln(III). For instance, ligand 11 is a stronger extractant than ligand 1 but displays similar selectivity trend across the Ln(III) series to that of ligand 3. The lower extraction strength of ligand 11 relative to ligand 3 can be attributed to a presence of longer alkyl substituents, which, similarly to ligands 5 and 6 in respect to ligand 3 (FIG. 4B), results in suppressed extraction power of DGA ligands. A reverse takes place when the linear N-alkyl substituents are extended beyond eight carbons, with ligand 12 in FIG. 2F serving as an example.

The extension of two N-alkyl groups in DGA by four carbons results in improved extraction of all Ln(III), which is counterintuitive to what has been presented above. There may be a change in performance when considering DGA ligands with linear N-alkyl substituents, likely TODGA (1) with four N-octyl substituents representing the turning point (FIG. 3A). While it is true that DGAs with shorter alkyl substituents (less then C8) are generally stronger extractants of Ln(III) then TODGA (1), mainly due to reduced steric hindrance around the metal binding site, a different mechanism appears to take place when the N-alkyl substituent length is increased beyond eight carbons, reversing the extraction trend.

Figure 3C:
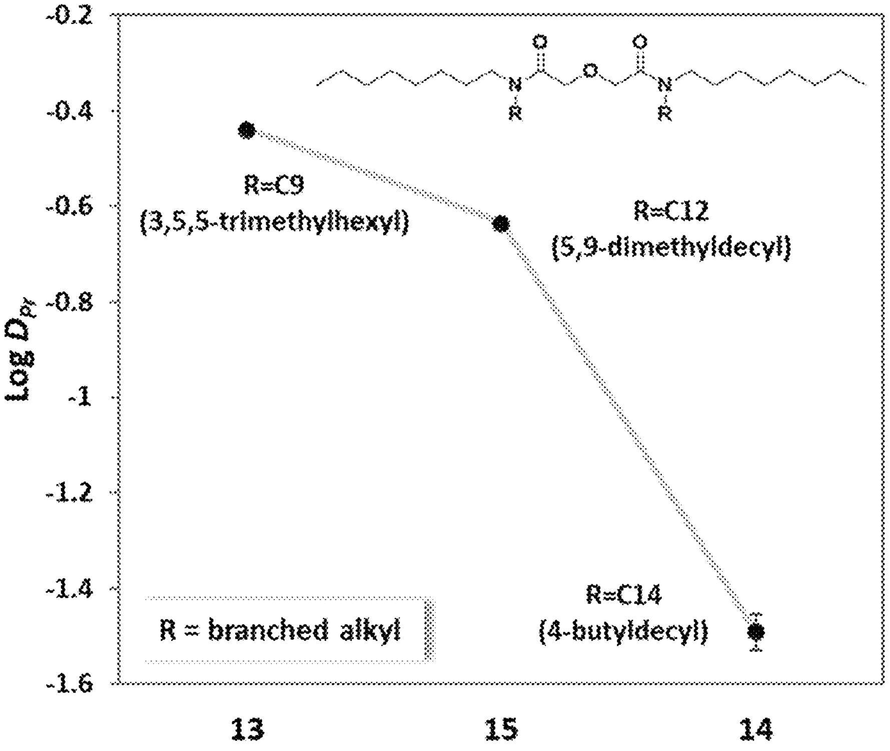

Notably, the N,N-di(2-ethylhexyl)-N',N'-dioctyldiglycolamide (DEHDODGA) in comparison to ligand 2 was shown to be ineffective in improving the extraction efficiency of Ln(III) from 1.5 M nitric acid ($D_{La}$=0.52 and $D_{Lu}$=3.40 vs. $D_{La}$=0.72 and $D_{Lu}$=6.35 using ligand 2). The placement of the branching point on an N-alkyl substituent further away from the metal ion binding site (from β to γ, δ, or ε position) has a profound positive effect on DGA's performance and results in improved D ratios and selectivity profile across the Ln(III) series relative to ligand 2 (FIG. 3C).

Figure 2G:
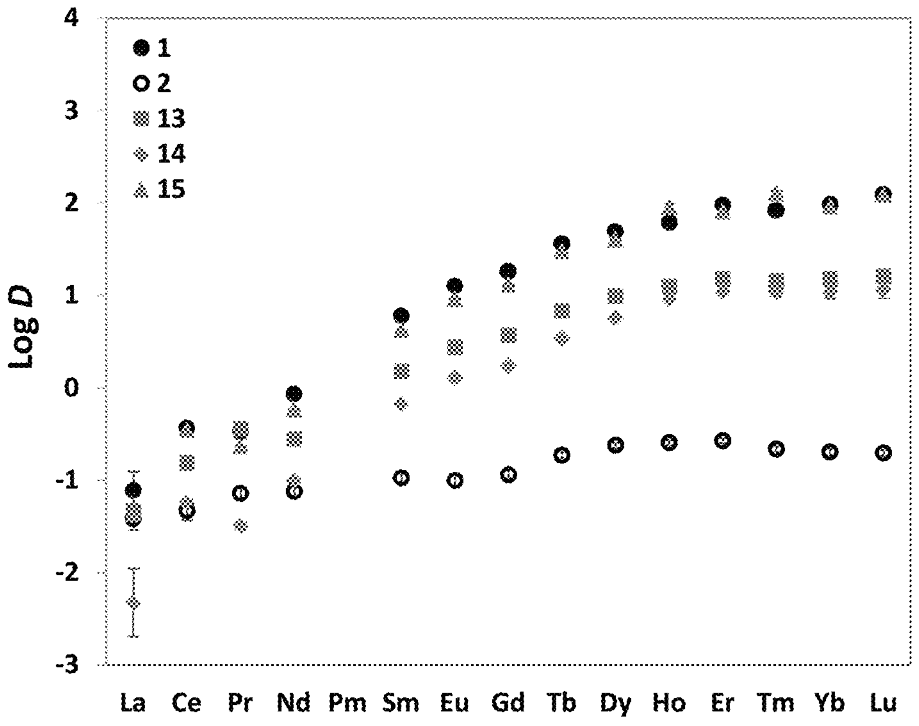
Figure 2H:
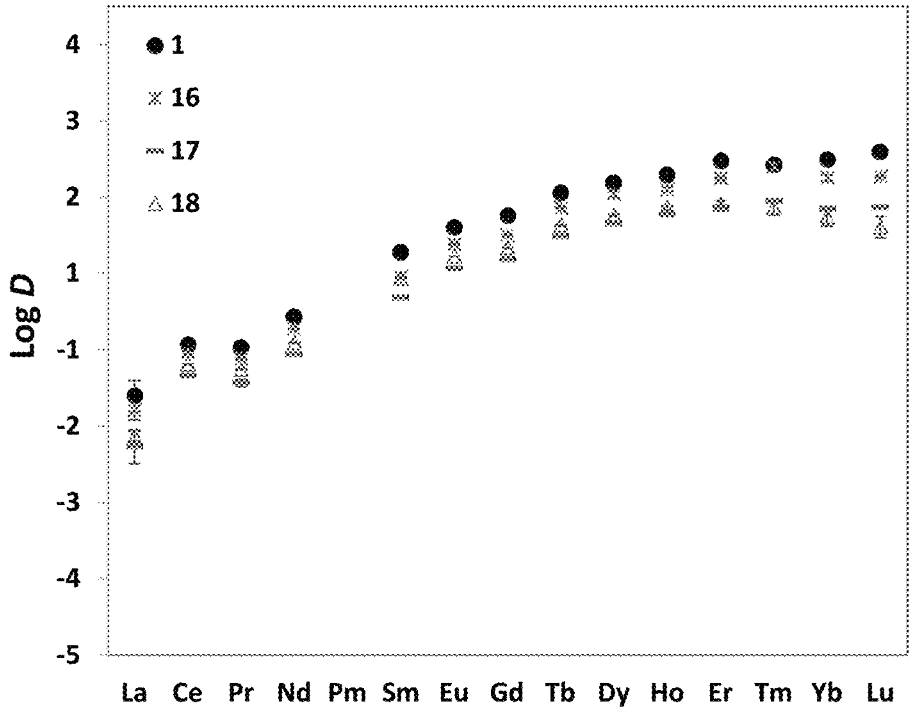
Figure 4C:
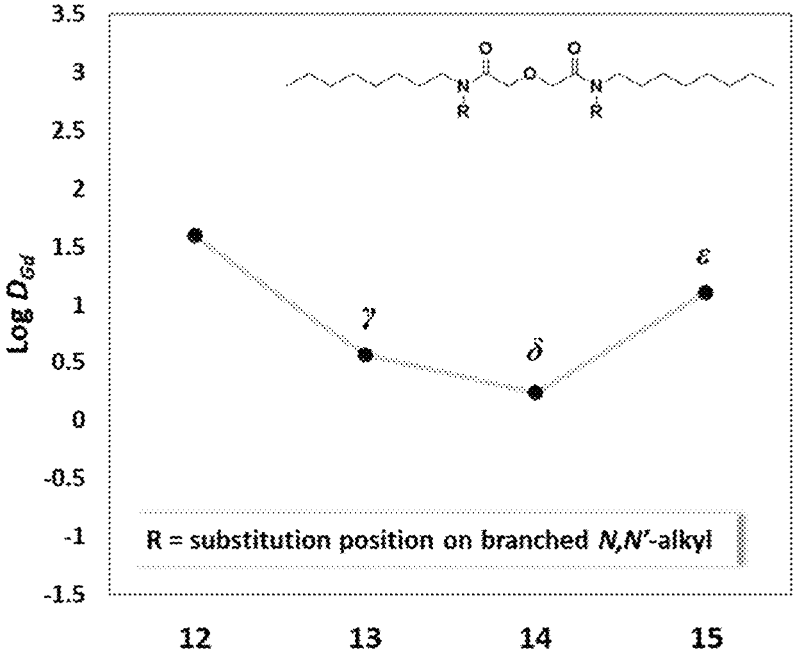

Even though ligands 13, 14, and 15 are not isostructural, due to inaccessibility of such branched 10 amines, halides, aldehydes, or alcohols required for the synthesis, they show a notable change in separation of Ln(III). As shown in FIGS. 2G and 4C, the ligands 13 and 14 with branching at γ and δ sites, respectively, are weaker extractants than ligands 1 and 12, likely due to closer proximity of these tertiary carbon sites to the metal ion binding site. When the tertiary carbon site is farthest from the amide nitrogen atom, as in ligand 15, extraction strength and selectivity increase and resemble that of ligand 1. Ligands 12 and 15 are isostructural, each have two n-octyl and two $C_{12}H_{25}$ N-substituents, and even though their performance is comparable (FIG. 4C and Table 1), the less bulky ligand 12 extracts Ln(III) more efficiently. This ligand-pair, in particular, demonstrates that subtle changes to the ligand's structure have a significant impact on its performance in Ln(III) separation.

Figure 5:
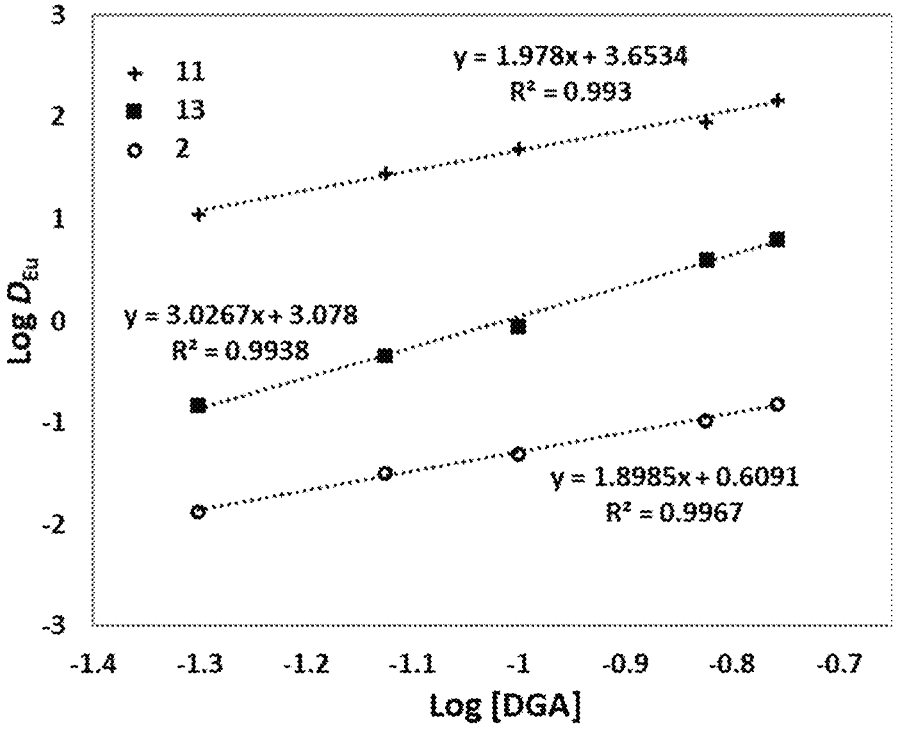
FIG. 5 is a graph showing Eu extraction capability of ligands 2, 11, and 13 from 3M HCl solution into Isopar L with 30 vol % of Exxal 13 at 25° C. Concentration of Eu in the acidic solution is 1.2 mM.

FIG. 5 plots data useful for determining the stoichiometry of extracted species for new lipophilic ligands 11 and 13. The results suggest that ligand 13 similarly to ligand 1 forms 3:1 ligand to Eu(III) complexes in the organic phase, whereas 2:1 species are formed with ligands 2 and 11. The result for ligand 11 is unexpected since it is a substrate with substantially reduced steric hindrance around the three O-donor binding site, similar to ligand 3.

While there have been shown and described what are at present considered the preferred embodiments of the invention, those skilled in the art may make various changes and modifications which remain within the scope of the invention defined by the appended claims.

What is claimed is:

1. A method for extracting rare earth elements from aqueous solution, the method comprising:

(i) acidifying an aqueous solution containing said rare earth elements with an inorganic acid to result in an acidified aqueous solution containing said rare earth elements and containing the inorganic acid in a concentration of 1-12 M, wherein said rare earth elements are selected from lanthanides, actinides, or combination thereof; and (ii) contacting the acidified aqueous solution with an aqueous-insoluble hydrophobic solution comprising a rare earth extractant compound dissolved in an aqueous-insoluble hydrophobic solvent, to result in extraction of one or more of the rare earth elements into the aqueous-insoluble hydrophobic solution by binding of the rare earth extractant compound to the one or more rare earth elements, wherein the rare earth extractant compound is selected from the group consisting of the following structures:

15

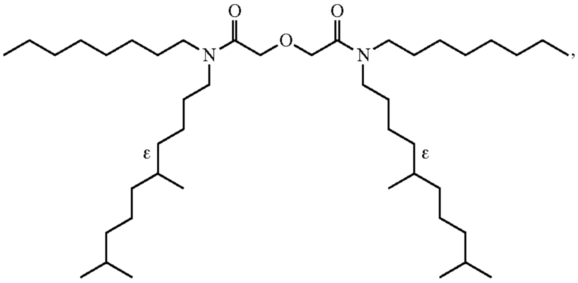

16

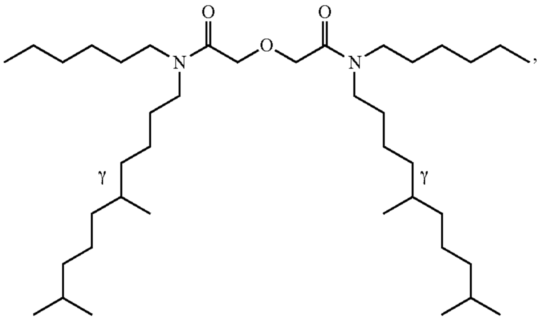

, and

17

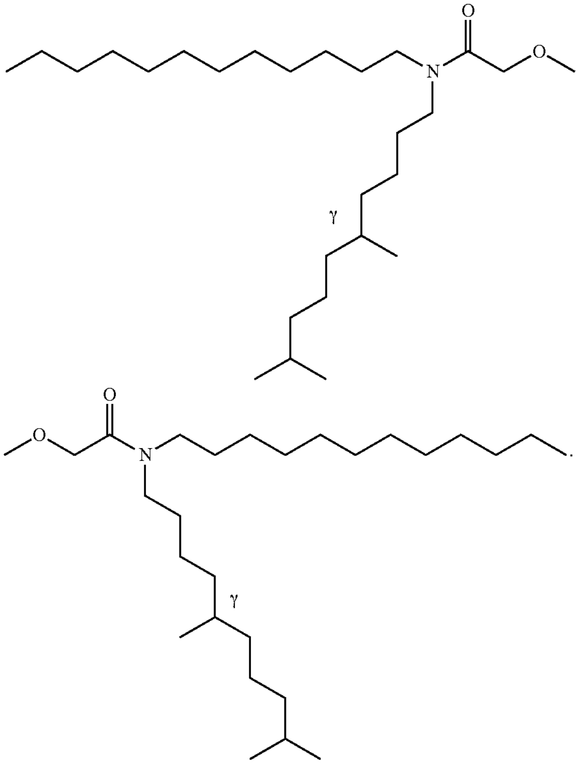

2. The method of claim 1, wherein the acidified aqueous solution contains the inorganic acid in a concentration of 1-8 M.

3. The method of claim 1, wherein the acidified aqueous solution contains the inorganic acid in a concentration of 2-6 M.

4. The method of claim 1, wherein the inorganic acid is a hydrohalide.

5. The method of claim 4, wherein the hydrohalide is hydrochloric acid.

6. The method of claim 1, wherein the aqueous solution contains at least one lanthanide element and at least one actinide element, and the method extracts one or more lanthanide elements to a greater extent than one or more actinide elements.

7. The method of claim 6, wherein said one or more actinide elements are at least one of thorium and uranium.

8. The method of claim 1, wherein said method further comprises:

(iii) stripping one or more rare earth elements from the aqueous-insoluble hydrophobic solution by contacting the aqueous-insoluble hydrophobic solution with an aqueous stripping solution containing an inorganic acid in a concentration of no more than 4 M, and provided that the concentration of inorganic acid in the aqueous stripping solution is at least 0.5 M less than the concentration of inorganic acid in the aqueous solution in step (i).

9. The method of claim 8, wherein step (iii) strips one or more lighter lanthanide elements from the aqueous-insoluble hydrophobic solution to a greater extent than one or more heavier lanthanide elements.

* * * * *